(12) United States Patent
Ouchi

(10) Patent No.: US 9,307,890 B2
(45) Date of Patent: Apr. 12, 2016

(54) ENDOSCOPIC FLUID PASSAGE CHANGEOVER VALVE UNIT AND ENDOSCOPE

(71) Applicant: OLYMPUS CORPORATION, Tokyo (JP)

(72) Inventor: Naoya Ouchi, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 45 days.

(21) Appl. No.: 14/326,162

(22) Filed: Jul. 8, 2014

(65) Prior Publication Data

US 2015/0011831 A1    Jan. 8, 2015

Related U.S. Application Data

(63) Continuation of application No. PCT/JP2013/080619, filed on Nov. 13, 2013.

(30) Foreign Application Priority Data

Nov. 21, 2012    (JP) .................................. 2012-255561

(51) Int. Cl.
*A61B 1/12*    (2006.01)
*A61B 1/00*    (2006.01)
(Continued)

(52) U.S. Cl.
CPC .......... *A61B 1/00068* (2013.01); *A61B 1/00091* (2013.01); *A61B 1/00114* (2013.01); *A61B 1/00128* (2013.01); *A61B 1/015* (2013.01); *A61B 1/07* (2013.01)

(58) Field of Classification Search
CPC ........... A61B 1/00068; A61B 1/00121; A61B 1/00128; A61B 1/125; A61M 1/0041; A61M 1/0043; F04B 1/2021; F04B 1/20

USPC .......... 600/154, 159; 604/33, 167.02, 167.03, 604/167.06, 256

See application file for complete search history.

(56) References Cited

U.S. PATENT DOCUMENTS 3,958,566 A * 5/1976 Furihata ............. A61B 1/00068
                                                    137/605
4,198,958 A * 4/1980 Utsugi ............... A61B 1/00068
                                                    600/154

(Continued)

FOREIGN PATENT DOCUMENTS

JP    A-61-143032    6/1986
JP    A-64-002620    1/1989

(Continued)

OTHER PUBLICATIONS

Dec. 17, 2013 International Search Report issued in International Application No. PCT/JP2013/080619 (with translation).

(Continued)

*Primary Examiner* — Anhtuan T Nguyen
*Assistant Examiner* — Jae Woo
(74) *Attorney, Agent, or Firm* — Oliff PLC

(57) ABSTRACT

In an endoscopic fluid passage changeover valve unit, a communication passage is formed in a shaft, the communication passage being opened to a hollow portion of a cylinder portion in an inside opening located on an outer peripheral surface of the shaft, and a seal member is provided at an angular position apart from the inside opening in circumferential directions of the cylinder portion. The shaft and the seal member are rotatable relative to the cylinder portion around a movement axis toward a position where a first upstream-side fluid passage is blocked by the seal member and toward a position where the inside opening of the communication passage faces the first upstream-side fluid passage.

20 Claims, 10 Drawing Sheets

(51) Int. Cl.
*A61B 1/015* (2006.01)
*A61B 1/07* (2006.01)

(56) References Cited

U.S. PATENT DOCUMENTS

| | | | | |
|---|---|---|---|---|
| 4,361,138 A * | 11/1982 | Kinoshita | ............ | A61B 1/00068 600/159 |
| 4,408,598 A * | 10/1983 | Ueda | ............ | A61B 1/12 600/159 |
| 4,537,209 A * | 8/1985 | Sasa | ............ | A61B 1/00137 134/102.1 |
| 4,561,428 A * | 12/1985 | Konomura | ............ | A61B 1/12 600/159 |
| 4,667,691 A * | 5/1987 | Sasa | ............ | A61B 1/125 134/168 R |
| 4,748,970 A * | 6/1988 | Nakajima | ............ | A61B 1/00068 600/113 |
| 4,765,312 A * | 8/1988 | Sasa | ............ | A61B 1/00068 600/153 |
| 4,775,365 A * | 10/1988 | Swartz | ............ | A61B 17/32002 137/625.22 |
| 4,800,869 A * | 1/1989 | Nakajima | ............ | A61B 1/00068 600/158 |
| 4,865,018 A * | 9/1989 | Kanno | ............ | H04N 17/002 348/72 |
| 4,884,133 A * | 11/1989 | Kanno | ............ | A61B 1/00059 348/68 |
| 5,147,333 A * | 9/1992 | Raines | ............ | A61M 39/02 137/625.34 |
| 5,376,071 A * | 12/1994 | Henderson | ............ | A61M 25/0606 604/115 |
| 5,749,829 A * | 5/1998 | Yokoi | ............ | A61B 1/00068 600/153 |
| 5,840,016 A * | 11/1998 | Kitano | ............ | A61B 1/12 251/335.2 |
| 6,254,529 B1 * | 7/2001 | Ouchi | ............ | A61B 1/00137 600/154 |
| 6,346,075 B1 * | 2/2002 | Arai | ............ | A61B 1/015 600/159 |
| 6,425,535 B1 * | 7/2002 | Akiba | ............ | A61B 1/00068 134/21 |
| 8,231,523 B2 * | 7/2012 | Uesugi | ............ | A61B 1/00068 600/118 |
| 2006/0264995 A1 * | 11/2006 | Fanton | ............ | A61B 17/32002 606/180 |
| 2006/0269421 A1 * | 11/2006 | Sakikawa | ............ | F04B 1/2021 417/53 |
| 2012/0088973 A1 * | 4/2012 | Morimoto | ............ | A61B 1/00068 600/156 |
| 2013/0060205 A1 * | 3/2013 | Mansour | ............ | A61M 39/223 604/248 |
| 2013/0303844 A1 * | 11/2013 | Grudo | ............ | A61B 1/00068 600/101 |
| 2014/0276215 A1 * | 9/2014 | Nelson | ............ | A61M 39/225 600/573 |
| 2014/0288372 A1 * | 9/2014 | Ando | ............ | G02B 23/2476 600/159 |

FOREIGN PATENT DOCUMENTS

| | | |
|---|---|---|
| JP | S648391 A | 1/1989 |
| JP | U-1-65004 | 4/1989 |
| JP | A-06-105802 | 4/1994 |
| JP | H06-108502 A | 4/1994 |
| JP | A-2003-052621 | 2/2003 |
| JP | A-2003-135391 | 5/2003 |

OTHER PUBLICATIONS

Sep. 16, 2014 Office Action issued in Japanese Application No. 2014-528755.
Jun. 4, 2015 International Preliminary Report on Patentability issued in International Application No. PCT/JP2013/080619.

* cited by examiner

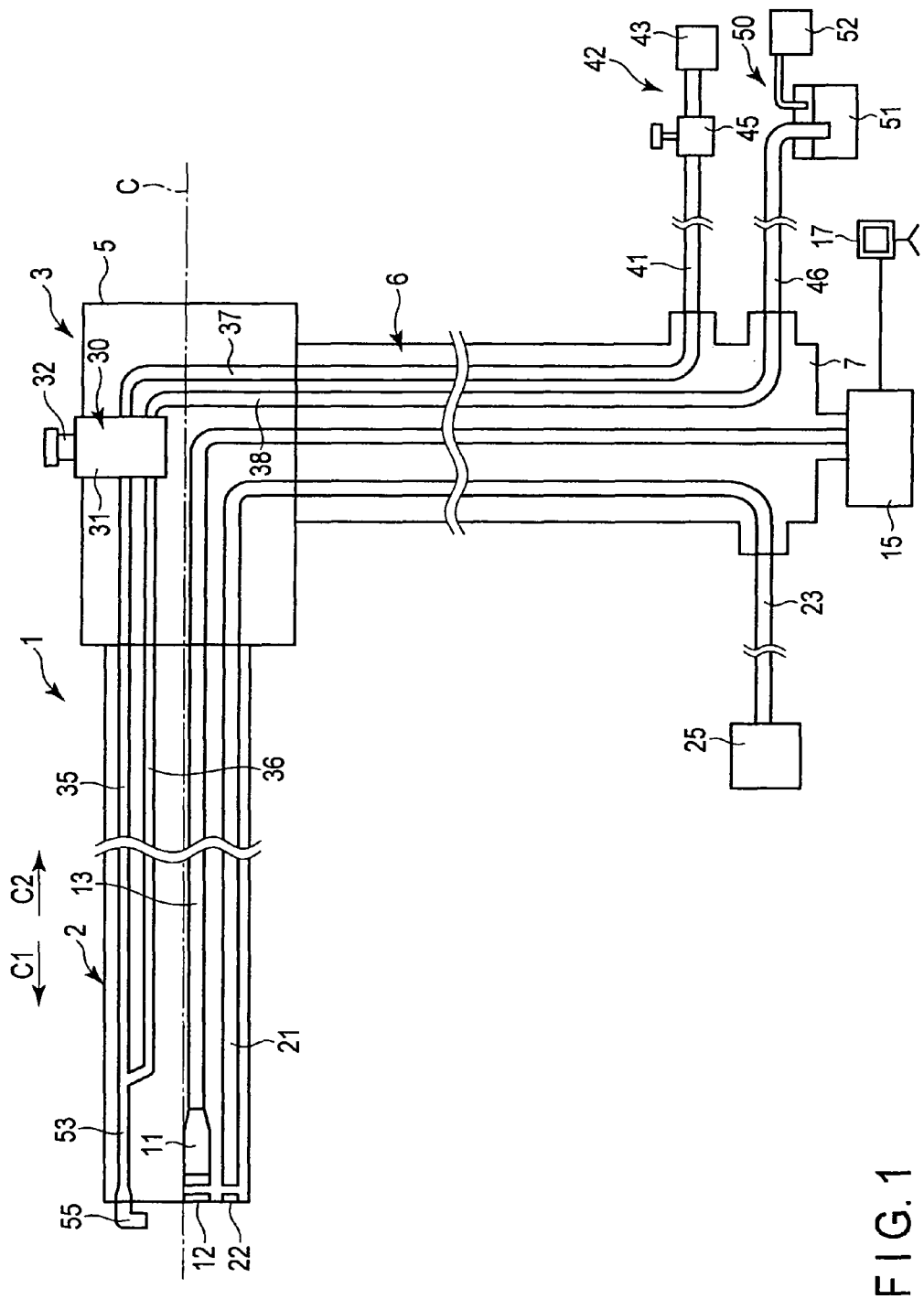
F I G. 1

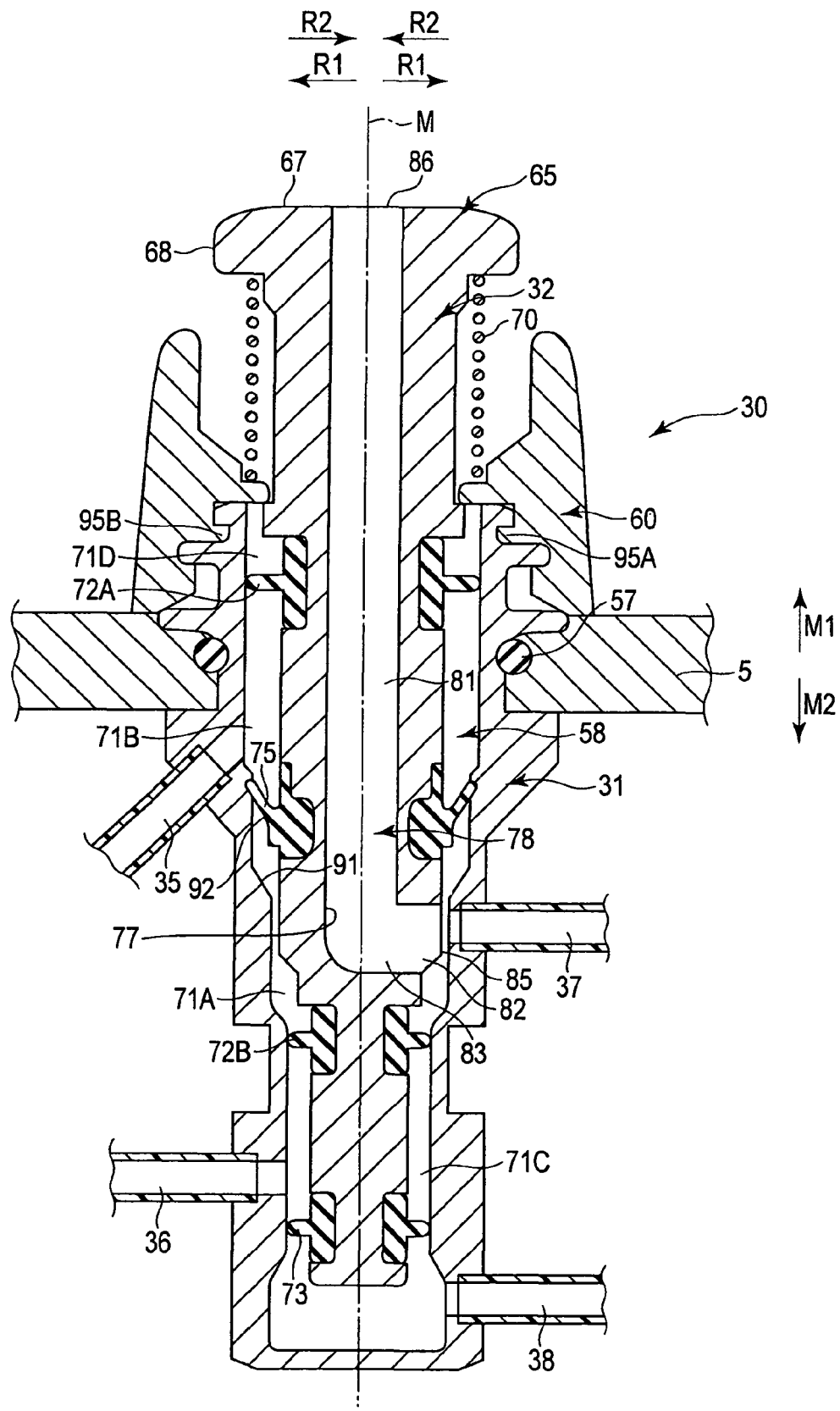
F I G. 3

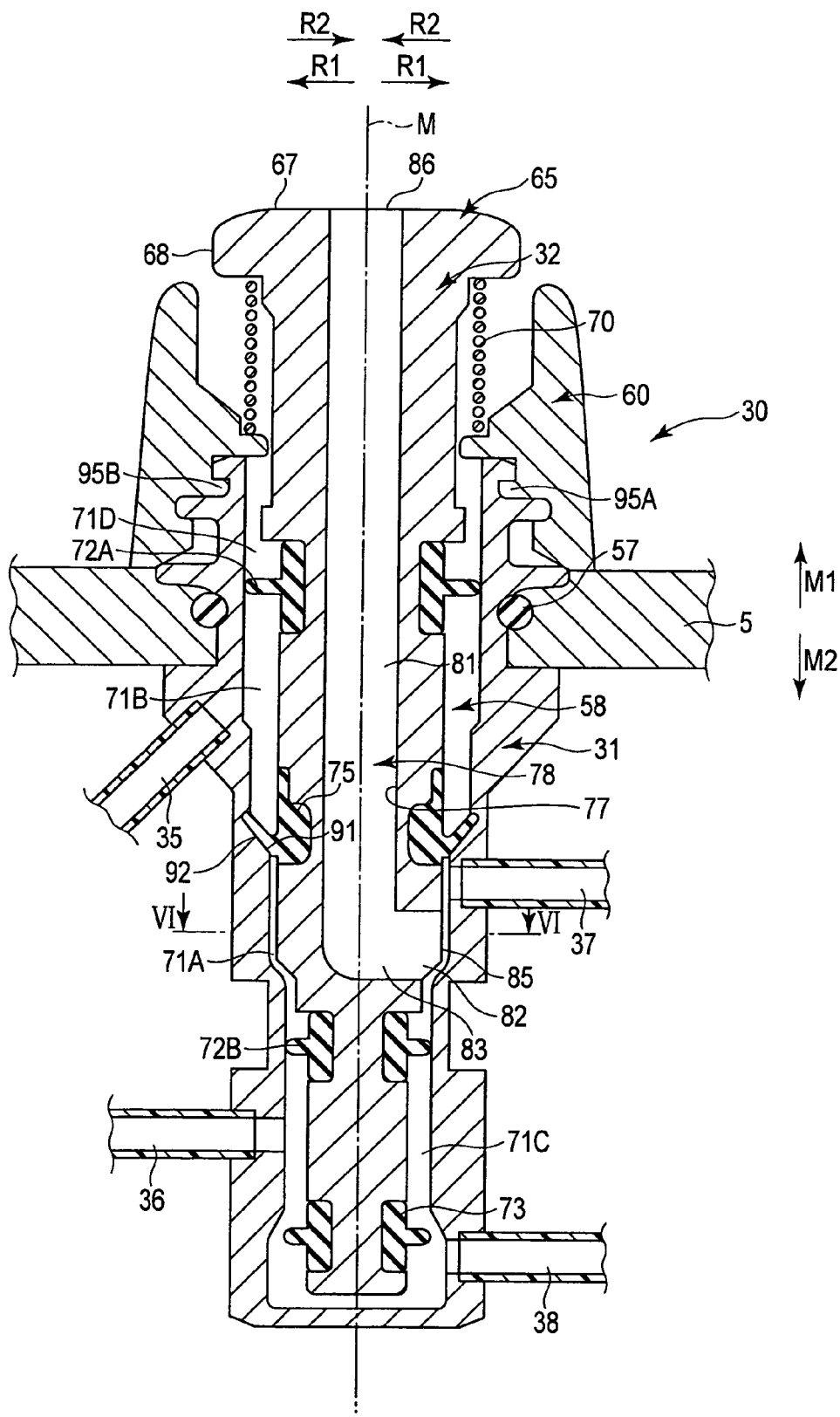
F I G. 4

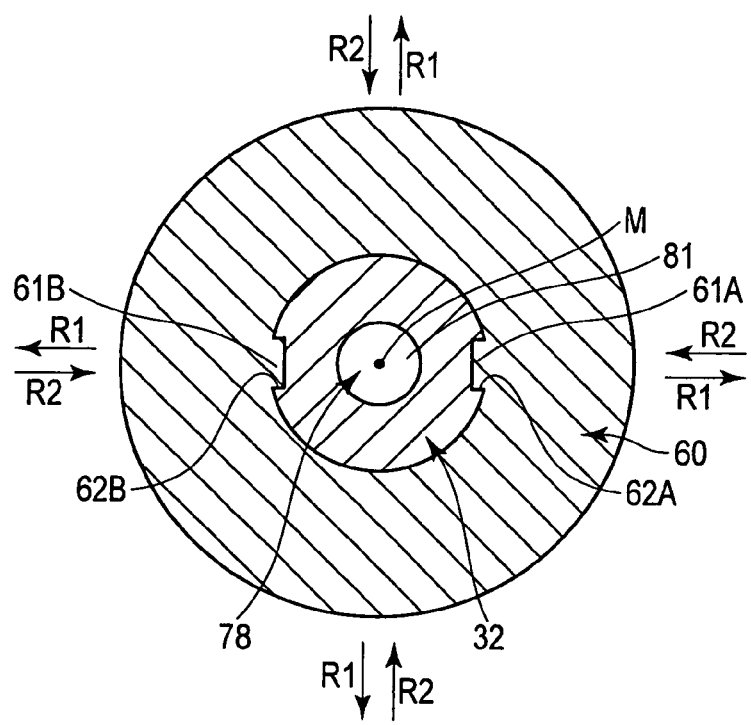
F I G. 5
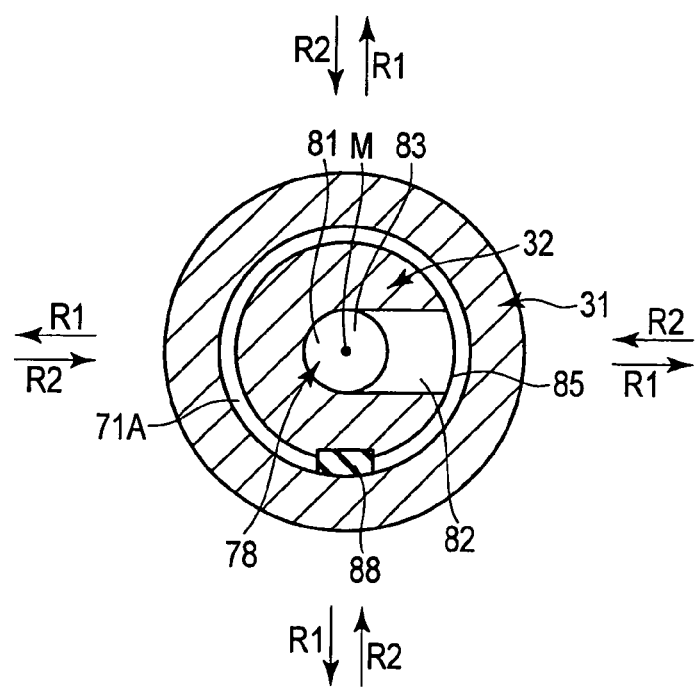
F I G. 6

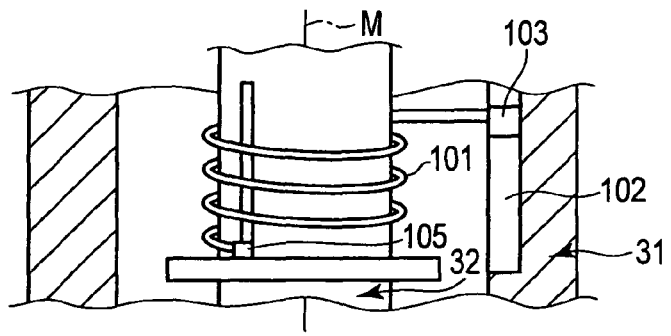
F I G. 13
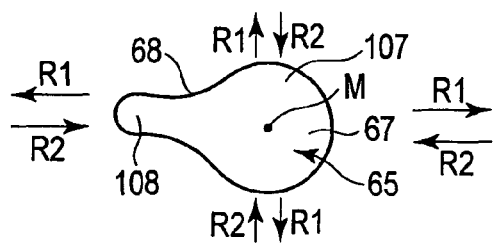
F I G. 14
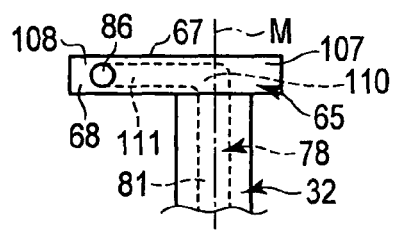
F I G. 15
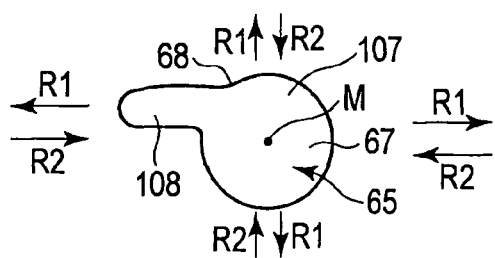
F I G. 16

ENDOSCOPIC FLUID PASSAGE CHANGEOVER VALVE UNIT AND ENDOSCOPE

CROSS-REFERENCE TO RELATED APPLICATIONS

This is a Continuation Application of PCT Application No. PCT/JP2013/080619, filed Nov. 13, 2013 and based upon and claiming the benefit of priority from prior Japanese Patent Application No. 2012-255561, filed Nov. 21, 2012, the entire contents of which are incorporated herein by reference.

BACKGROUND OF THE INVENTION

1. Field of the Invention

The present invention relates to an endoscopic fluid passage changeover valve unit which includes a cylinder portion having a hollow portion formed therein and which changes, in a region located to a downstream direction side from the hollow portion, fluid passages to supply a fluid that has passed through the hollow portion. The present invention also relates to an endoscope including this endoscopic fluid passage changeover valve unit.

2. Description of the Related Art

Jpn. Pat. Appln. KOKAI Publication No. 2003-52621 and Jpn. Pat. Appln. KOKAI Publication No. 64-2620 have each disclosed an endoscope in which a gas (air, carbon dioxide) and water are supplied as fluids to a distal portion of an insertion section. In each endoscope, an endoscopic fluid passage changeover valve unit is attached to a holding casing of an operation section. The endoscopic fluid passage switching valve unit includes a cylinder portion fixedly attached to the holding casing, and a shaft attached to the cylinder portion to be inserted in a hollow portion formed in the cylinder portion. The shaft is movable relative to the cylinder portion along a movement axis. A downstream end of an upstream-side gas supply passage and an upstream end of a downstream-side gas supply passage are in communication with the hollow portion, and a downstream end of an upstream-side water supply passage and an upstream end of a downstream-side water supply passage are in communication with the hollow portion. A communication passage which communicates the hollow portion with an outside of the holding casing is formed in the shaft, and the communication passage is open to the outside of the holding casing through an opening. In the hollow portion, the upstream-side gas supply passage, the downstream-side gas supply passage, and the communication passage are not in communication with the upstream-side water supply passage and the downstream-side water supply passage.

In Jpn. Pat. Appln. KOKAI Publication No. 2003-52621, the shaft is movable relative to the cylinder portion along the movement axis between a first input mode and a second input mode. In the first input mode, the communication between the upstream-side water supply passage and the downstream-side water supply passage is blocked in the hollow portion. Therefore, in the first input mode, water is not supplied to the downstream-side water supply passage from the upstream-side water supply passage. In the first input mode, the upstream-side air supply passage is in communication with the downstream-side air supply passage and the communication passage in the hollow portion. Here, when the opening of the communication passage is not blocked by, for example, a finger of a surgeon in the first input mode, the air which has passed through the upstream-side air supply passage flows to the outside of the holding casing from the opening through the communication passage. In this case, the air is not supplied to the downstream-side gas supply passage from the upstream-side gas supply passage. On the other hand, when the opening of the communication passage is blocked by, for example, the finger of the surgeon in the first input mode, air is supplied to the downstream-side gas supply passage from the upstream-side gas supply passage, and the air supply is performed in the downstream-side gas supply passage.

The shaft is then moved toward an axially parallel inward direction from the first input mode, and is thereby set in the second input mode. In the second input mode, the communication of the upstream-side air supply passage with the downstream-side air supply passage and the communication passage is blocked in the hollow portion. Therefore, in the second input mode, air is not supplied to the downstream-side gas supply passage and the communication passage from the upstream-side gas supply passage. In the second input mode, the upstream-side water supply passage is in communication with the downstream-side water supply passage in the hollow portion. Therefore, in the second input mode, water is supplied to the downstream-side water supply passage from the upstream-side water supply passage, and the water supply is performed in the downstream-side water supply passage.

In the endoscopic fluid passage changeover valve unit according to Jpn. Pat. Appln. KOKAI Publication No. 64-2620, two elastic springs extend parallel to each other along the movement axis. The two return springs are different in elastic constant from each other, and connect the cylinder portion to the shaft. Since the two elastic springs are provided, the shaft is movable relative to the cylinder portion along the movement axis between the first input mode and the second input mode and between the second input mode and a third input mode.

In the first input mode, the communication between the upstream-side water supply passage and the downstream-side water supply passage is blocked in the hollow portion. Therefore, in the first input mode, water is not supplied to the downstream-side water supply passage from the upstream-side water supply passage. In the first input mode, the communication of the upstream-side gas supply passage with the downstream-side gas supply passage and the communication passage is blocked in the hollow portion. Therefore, in the first input mode, carbon dioxide is not supplied to the downstream-side gas supply passage and the communication passage from the upstream-side gas supply passage. In this case, carbon dioxide does not flow to the outside of the holding casing from the opening.

The shaft is then moved toward the axially parallel inward direction from the first input mode, and is thereby set in the second input mode. In the second input mode, the communication between the upstream-side water supply passage and the downstream-side water supply passage is blocked in the hollow portion. Therefore, in the second input mode, water is not supplied to the downstream-side water supply passage from the upstream-side water supply passage. In the second input mode, the upstream-side gas supply passage is in communication with the downstream-side gas supply passage and the communication passage in the hollow portion. When the opening of the communication passage is closed by, for example, the finger of the surgeon in the second input mode, carbon dioxide is supplied to the downstream-side gas supply passage from the upstream-side gas supply passage, and a supply of carbon dioxide is performed in the downstream-side gas supply passage.

The shaft is then further moved toward the axially parallel inward direction from the second input mode, and is thereby set in the third input mode. In the third input mode, the communication of the upstream-side gas supply passage with the downstream-side gas supply passage and the communication passage is blocked in the hollow portion. Therefore, in the third input mode, carbon dioxide is not supplied to the downstream-side gas supply passage and the communication passage from the upstream-side gas supply passage. In the third input mode, the upstream-side water supply passage is in communication with the downstream-side water supply passage in the hollow portion. Therefore, in the third input mode, water is supplied to the downstream-side water supply passage from the upstream-side water supply passage, and the water supply is performed in the downstream-side water supply passage.

BRIEF SUMMARY OF THE INVENTION

According to one aspect of the invention, an endoscopic fluid passage changeover valve unit includes that: a cylinder portion having a hollow portion formed therein; a first upstream-side fluid passage which has a downstream end thereof located on an inner peripheral surface of the cylinder portion, and which is configured to supply a first fluid to the hollow portion from the downstream end; a shaft which extends along a movement axis to be inserted into the hollow portion, and inside which a communication passage is formed, the communication passage being opened to an outside of the cylinder portion through an opening and being also opened to the hollow portion in an inside opening located on an outer peripheral surface of the shaft; a first seal member which is provided on the outer peripheral surface of the shaft rotatably around the movement axis, and which is located at an angular position apart from the inside opening in circumferential directions of the cylinder portion; and a second seal member which attaches the shaft to the cylinder portion so that the shaft and the first seal member are rotatable relative to the cylinder portion around the movement axis toward a position where the downstream end of the first upstream-side fluid passage is blocked by the first seal member and toward a position where the inside opening of the communication passage faces the downstream end of the first upstream-side fluid passage.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a schematic diagram showing the configuration of an endoscope according to a first embodiment;

FIG. 3 is a sectional view schematically showing the configuration of the endoscopic fluid passage changeover valve unit in a second input mode according to the first embodiment;

FIG. 4 is a sectional view schematically showing the configuration of the endoscopic fluid passage changeover valve unit in a third input mode according to the first embodiment;

FIG. 5 is a sectional view taken along the line V-V of FIG. 2;

FIG. 6 is a sectional view taken along the line VI-VI of FIG. 4;

FIG. 13 is a schematic diagram showing a configuration in which a cylinder portion and a piston portion are connected by a torsional spring according to the second embodiment;

FIG. 14 is a schematic diagram showing an operation input button of the piston portion as seen from an axially parallel outward direction according to a third embodiment;

FIG. 15 is a schematic diagram showing the operation input button of the piston portion as seen from a diametrically outer peripheral direction according to the third embodiment; and FIG. 16 is a schematic diagram showing the operation input button of the piston portion as seen from the axially parallel outward direction according to a modification of the third embodiment.

DETAILED DESCRIPTION OF THE INVENTION

First Embodiment

Figure 2:
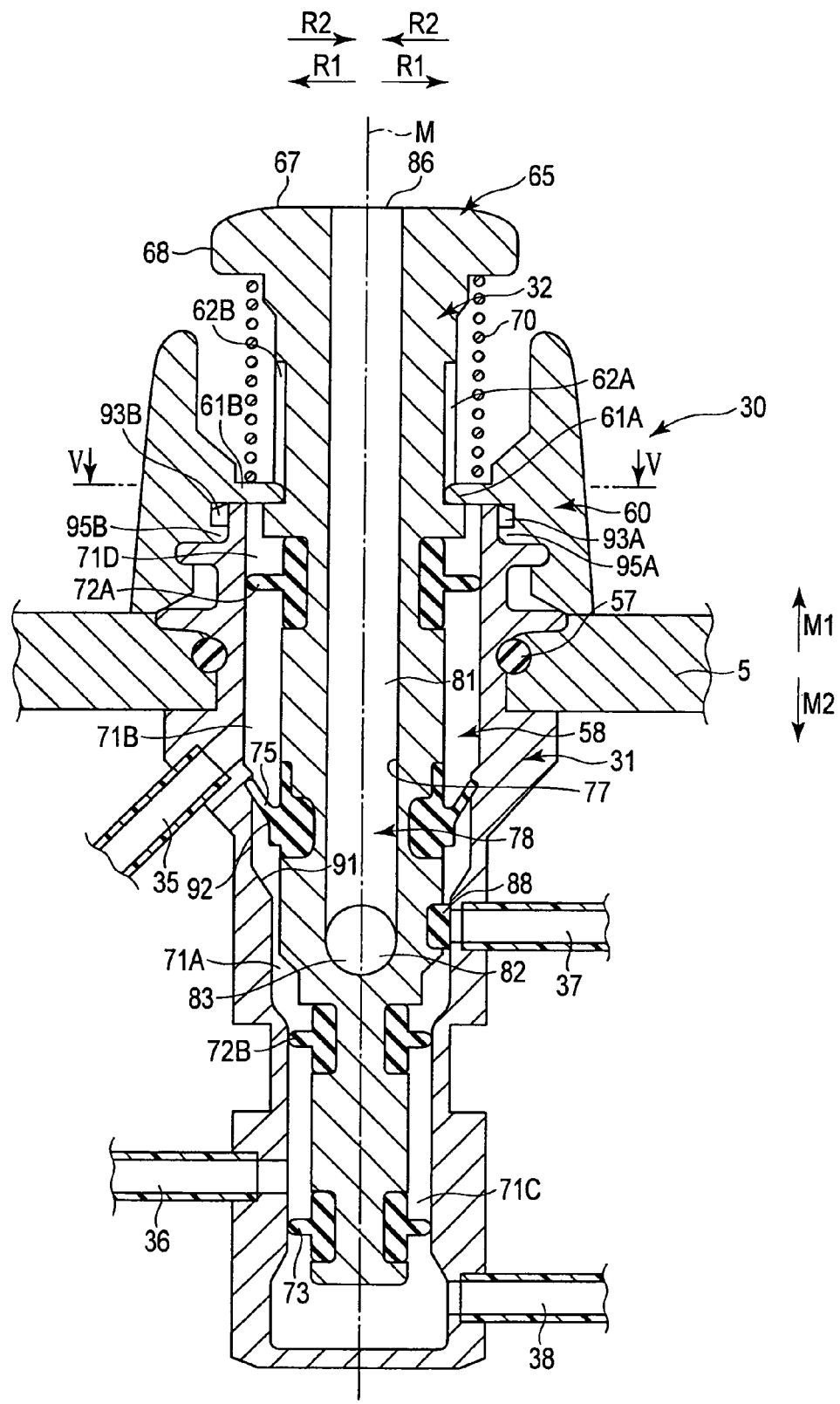
FIG. 2 is a sectional view schematically showing the configuration of an endoscopic fluid passage changeover valve unit in a first input mode according to the first embodiment.

A first embodiment of the present invention is described with reference to FIG. 1 to FIG. 9. FIG. 1 is a diagram showing an endoscope 1 according to the first embodiment. As shown in FIG. 1, the endoscope 1 has a longitudinal axis C. One of directions parallel to the longitudinal axis C is a distal direction (the direction of an arrow C1 in FIG. 1), and a direction opposite to the distal direction is a proximal direction (the direction of an arrow C2 in FIG. 1).

The endoscope 1 includes an insertion section 2 extending along the longitudinal axis C, and an operation section 3 provided to the proximal direction side with respect to the insertion section 2. The operation section 3 includes a holding casing 5 serving as an exterior. One end of a universal cord 6 is connected to the operation section 3. A scope connector 7 is provided in the other end of the universal cord 6.

An image pickup element 11 such as a CCD is incorporated in a distal portion of the insertion section 2. The image pickup element 11 is configured to image a subject through an observation window 12 provided on a distal face of the insertion section 2. One end of an imaging cable 13 is connected to the image pickup element 11. The imaging cable 13 extends through an inside of the insertion section 2, an inside of the operation section 3, and an inside of the universal cord 6. The other end of the imaging cable 13 is connected to an image processor 15 which is an image processing unit by the scope connector 7. The image processor 15 is electrically connected to a monitor 17 which is a display unit. A subject figure imaged by the image pickup element 11 is subjected to image processing by the image processor 15, and displayed on the monitor 17.

A light guide 21 extends through the inside of the insertion section 2 along the longitudinal axis C. One end of the light guide 21 is optically connected to an illumination window 22 provided on the distal face of the insertion section 2. The light guide 21 extends the inside of through the insertion section 2, the inside of the operation portion 3, and the inside of the universal cord 6. The other end of the light guide 21 is optically connected to one end of a light guide tube 23 by the scope connector 7. The other end of the light guide tube 23 is connected to a light source 25. Light emitted from the light source 25 is applied to the subject from the illumination window 22 through the light guide tube 23 and the light guide 21.

An endoscopic fluid passage changeover valve unit 30 is attached to the holding casing 5 of the operation section 3. The endoscopic fluid passage changeover valve unit 30 includes a cylinder portion 31 fixedly attached to the holding casing 5, and a piston portion 32 which is a shaft attached to the cylinder portion 31.

A downstream-side gas supply passage 35 which is a first downstream-side fluid passage and a downstream-side water supply passage 36 which is a second downstream-side fluid passage extend through the inside of the insertion section 2 along the longitudinal axis C. The downstream-side gas supply passage 35 and the downstream-side water supply passage 36 are parts of the endoscopic fluid passage switching valve unit 30, and upstream ends of the downstream-side air supply passage 35 and the downstream-side water supply passage 36 extend up to the cylinder portion 31.

An upstream-side gas supply passage 37 which is a first upstream-side fluid passage and an upstream-side water supply passage 38 which is a second upstream-side fluid passage extend through the inside of the operation portion 3 and the inside of the universal cord 6. The upstream-side air supply passage 37 and the upstream-side water supply passage 38 are parts of the endoscopic fluid passage changeover valve unit 30, and downstream ends of the upstream-side gas supply passage 37 and the upstream-side water supply passage 38 extend up to the cylinder portion 31.

The upstream end of the upstream-side gas supply passage 37 is connected to a downstream end of a gas supply tube 41 by the scope connector 7. A upstream end of the gas supply tube 41 is connected to a gas supply source 42. The gas supply source 42 includes a gas tank 43 configured to store a gas such as air or carbon dioxide, and an on-off valve 45. If the open-or-close valve 45 is opened, a gas which is a first fluid is supplied from the gas tank 43 through the gas supply tube 41 and the upstream-side gas supply passage 37.

A upstream end of the upstream-side water supply passage 38 is connected to a downstream end of a water supply tube 46 by the scope connector 7. A upstream end of the water supply tube 46 is connected to a water supply source 50. The water supply source 50 includes a water tank 51 configured to store water, and a pump 52. If the pump 52 is driven, the water which is a second fluid different from the first fluid is supplied from the water tank 51 through the water supply tube 46 and the upstream-side water supply passage 38.

A junction flow passage 53 where the downstream-side gas supply passage 35 and the downstream-side water supply passage 36 join together is provided in the distal portion of the insertion section 2. The gas supplied to the downstream-side gas supply passage 35 from the upstream-side gas supply passage 37 is discharged from a nozzle 55 provided on the distal face of the insertion section 2 through the junction flow passage 53. The water supplied to the downstream-side water supply passage 36 from the upstream-side water supply passage 38 is ejected from the nozzle 55 through the junction flow passage 53. In the upstream-side gas supply passage 37, the downstream-side gas supply passage 35, and the gas supply tube 41, a direction toward the nozzle 55 is the downstream direction, and a direction toward the gas supply source 42 is the upstream direction. In the upstream-side water supply passage 38, the downstream-side water supply passage 36, and the water supply tube 46, a direction toward the nozzle 55 is the downstream direction, and a direction toward the water supply source 50 is the upstream direction.

FIG. 2 to FIG. 4 are diagrams showing the configuration of the endoscopic fluid passage changeover valve unit 30. As shown in FIG. 2 to FIG. 4, the cylinder portion 31 is fixed to the holding casing 5 via a packing member 57. A hollow portion 58 is formed inside the cylinder portion 31. The piston portion 32 which is the shaft is attached to the cylinder portion 31 via a connection cap 60 which is a cylindrical intermediary member. The piston portion 32 extends along a movement axis M. The piston portion 32 is attached to the cylinder portion 31 to be inserted in the hollow portion 58.

Here, one of directions parallel to the movement axis M is an axially parallel outward direction (the direction of an arrow M1 in FIG. 2 to FIG. 4), and the other direction parallel to the movement axis M is an axially parallel inward direction (the direction of an arrow M2 in FIG. 2 to FIG. 4). That is, the axially parallel outward direction is a direction toward an outside of the holding casing 5 along the movement axis M, and the axially parallel inward direction is a direction toward an inside of the holding casing 5 along the movement axis M. A direction to depart from the movement axis M in a plane perpendicular to the movement axis M is a diametrically outer peripheral direction (the direction of an arrow R1 in FIG. 2 to FIG. 4), and the direction toward the movement axis M in the section perpendicular to the movement axis M is a diametrically inner peripheral direction (the direction of an arrow R2 in FIG. 2 to FIG. 4). The diametrically outer peripheral direction and the diametrically inner peripheral direction are cylinder diametrical directions.

FIG. 5 is a sectional view taken along the line V-V of FIG. 2. As shown in FIG. 2 to FIG. 5, the connection cap 60 is provided with engagement protrusions 61A and 61B projecting toward the diametrically inner peripheral direction. The engagement protrusions 61A and 61B are arranged about 180° apart from each other in directions around the movement axis (the circumferential directions of the cylinder portion 31). The piston portion 32 is provided with engagement slots 62A and 62B along the movement axis M. The engagement slots 62A and 62B are arranged about 180° apart from each other in the directions around the movement axis. When the corresponding engagement protrusion 61A or 61B is engaged with each of the engagement slots 62A and 62B, the piston portion 32 is attached to the connection cap 60. The position of the piston portion 32 relative to the connection cap 60 in the directions around the movement axis is set by the engagement protrusions 61A and 61B and the engagement slots 62A and 62B.

The engagement slots 62A and 62B are movable relative to the engagement protrusions 61A and 61B along the movement axis M. Thus, the piston portion 32 which is the shaft is movable relative to the cylinder portion 31 and the connection cap 60 along the movement axis M. The piston portion 32 is rotatable relative to the cylinder portion 31 around the movement axis M. Here, when the corresponding engagement protrusion 61A or 61B is engaged with each of the engagement slots 62A and 62B, the rotation of the connection cap 60 relative to the piston portion 32 around the movement axis M is regulated. Therefore, the connection cap 60 is rotatable relative to the cylinder portion 31 around the movement axis M together with the piston portion 32.

An operation input button 65 which is an operation input section is provided in an axially-parallel-outward-direction-side part of the piston portion 32. The operation input button 65 is exposed to the outside of the holding casing 5. When the operation input button 65 is pressed toward the axially parallel inward direction, a movement operation of moving the piston portion 32 along the movement axis M is input. When the operation input button 65 is rotated around the movement axis M, a rotation operation of rotating the piston portion 32 around the movement axis M is input. The operation input button 65 includes a first exposed surface 67 facing toward the axially parallel outward direction, and a second exposed surface 68 facing toward the diametrically outer peripheral direction.

Here, FIG. 2 shows a first input mode in which the rotation operation and the movement operation are not performed in the operation input button 65. FIG. 3 shows a second input mode in which the piston portion 32 has been rotated a predetermined rotation angle around the movement axis M from the first input mode by the rotation operation in the operation input button 65. In the present embodiment, the piston portion 32 is rotated relative to the cylinder portion 31 from the first input mode about 90° toward a clockwise direction when seen from the axially parallel outward direction, and is thereby set in the second input mode. Moreover, FIG. 4 shows a third input mode in which the piston portion 32 has moved a predetermined distance along the movement axis M from the first input mode or the second input mode by the movement operation in the operation input button 65. In the present embodiment, the piston portion 32 is moved relative to the cylinder portion 31 toward the axially parallel inward direction from the first input mode or the second input mode, and is thereby set in the third input mode. In FIG. 4, the piston portion 32 has moved in the axially parallel inward direction from the second input mode.

As shown in FIG. 2 to FIG. 4, an elastic spring 70 extends along the movement axis M in the endoscopic fluid passage changeover valve unit 30. The return spring 70 is located to the diametrically outer peripheral direction side of the piston portion 32. One end of the return spring 70 is connected to the operation input button 65 of the piston portion 32. The other end of the return spring 70 is connected to the connection cap 60. When the piston portion 32 is moved relative to the cylinder portion 31 and the connection cap 60 toward the axially parallel inward direction from the first input mode or the second input mode, the elastic spring 70 contracts. As a result, an urging force in the axially parallel outward direction is applied to the piston portion 32 from the return spring 70. Thus, when the operation input button 65 is released after the operation input button 65 has been pressed toward the axially parallel inward direction, the piston portion 32 returns to the position of the first input mode or the second input mode in directions parallel to the movement axis M in response to the urging force from the elastic spring 70.

Space portions 71A to 71D are formed between the cylinder portion 31 and the piston portion 32 in the cylinder diametrical directions. Seal members 72A and 72B, a seal member 73, and a valve member 75 are attached to the piston portion 32. The seal members 72A and 72B, the seal member 73, and the valve member 75 are movable relative to the cylinder portion 31 and the connection cap 60 along the movement axis M together with the piston portion 32. The seal members 72A and 72B, the seal member 73, and the valve member 75 are also rotatable relative to the cylinder portion 31 around the movement axis M together with the piston portion 32 and the connection cap 60.

The seal member 72A is located to the axially parallel outward direction side with respect to the valve member 75. The seal member 72B is located to the axially parallel inward direction side with respect to the valve member 75. The seal member 73 is located to the axially parallel inward direction side with respect to the seal member 72B. In each of the seal members 72A and 72B, the space between the cylinder portion 31 and the piston portion 32 is constantly kept airtight and watertight.

The first space portion 71A which is one of the space portions 71A to 71D is formed between the valve member 75 and the seal member 72B in the directions parallel to the movement axis M. The downstream end of the upstream-side gas supply passage 37 which is the first upstream-side fluid passage can be in communication with the first space portion 71A. Thus, in the upstream-side air supply passage 37, the gas which is the first fluid is supplied toward the first space portion 71A of the hollow portion 58.

The second space portion 71B which is one of the space portions 71A to 71D is formed between the valve member 75 and the seal member 72A in the directions parallel to the movement axis M. Therefore, the valve member 75 is located between the first space portion 71A and the second space portion 71B. The second space portion 71B can be in communication with the first space portion 71A through the valve member 75. The upstream end of the downstream-side gas supply passage 35 which is the first downstream-side fluid passage is in communication with the second space portion 71B. Thus, in the downstream-side air supply passage 35, the gas as the first fluid which has passed through the second space portion 71B of the hollow portion 58 is supplied.

The third space portion 71C which is one of the space portions 71A to 71D is formed in a part located to the axially parallel inward direction side with respect to the seal member 72B. The communication of the third space portion 71C with the first space portion 71A and the second space portion 71B is blocked by the seal member 72B. The downstream end of the upstream-side water supply passage 38 which is the second upstream-side fluid passage is in communication with the third space portion 71C. Thus, in the upstream-side water supply passage 38, the water which is the second fluid is supplied toward the third space portion 71C of the hollow portion 58. The upstream end of the downstream-side water supply passage 36 which is the second downstream-side fluid passage is in communication with the third space portion 71C. Thus, in the downstream water supply passage 36, the water as the second fluid which has passed through the third space portion 71C of the hollow portion 58 is sent. The seal member 73 is disposed in the third space portion 71C.

The fourth space portion 71D which is one of the space portions 71A to 71D is formed in a part located to the axially parallel outward direction side with respect to the seal member 72A. The communication of the fourth space portion 71D with the first space portion 71A and the second space portion 71B is blocked by the seal member 72A.

FIG. 6 is a sectional view taken along the line VI-VI of FIG. 4. As shown in FIG. 2 to FIG. 4 and FIG. 6, a communication passage 78 is defined by a passage defining portion 77 in the piston portion 32 which is the shaft. The communication passage 78 allows the communication between the first space portion 71A and the outside of the holding casing 5. The communication passage 78 includes an axially parallel passage portion 81 extending along the movement axis M, a diametrical passage portion 82 extending along the cylinder diametrical directions (the direction of an arrow R1 and the direction of an arrow R2 in FIG. 2 to FIG. 6), and a bent portion 83 provided between the axially parallel passage portion 81 and the diametrical passage portion 82. The diametrical passage portion 82 is opened with respect to the first space portion 71A at an inside opening 85. The axially parallel passage portion 81 is opened with respect to the outside of the holding casing 5 through an opening 86. The opening 86 is provided on the first exposed surface 67 of the operation input button 65.

A seal member 88 is attached to the piston portion 32 which is the shaft. The seal member 88 is rotatable relative to the cylinder portion 31 around the movement axis M together with the piston portion 32. The seal member 88 is located between the cylinder portion 31 and the piston portion 32 in the cylinder diametrical directions. The seal member 88 is also located between the valve member 75 and the seal member 72B in the directions parallel to the movement axis M. Therefore, the seal member 88 is located in the first space portion 71A. The seal member 88 is disposed at an angular position apart from the inside opening 85 in the directions around the movement axis (the circumferential directions of the cylinder portion 31). In the present embodiment, the seal member 88 is disposed at an angular position apart from the inside opening 85 by about 90° toward the clockwise direction when seen from the axially parallel outward direction.

As shown in FIG. 2, in the first input mode, the seal member 88 is disposed to face the upstream-side gas supply passage 37 in the first space portion 71A. Thus, in the first input mode, the communication between the upstream-side gas supply passage 37 and the first space portion 71A is blocked by the seal member 88. Therefore, in the first input mode, the gas does not flow into the first space portion 71A from the upstream-side gas supply passage 37, and the gas is not supplied to the downstream-side gas supply passage 35 from the upstream-side gas supply passage 37. In the first input mode, the gas is not supplied to the communication passage 78 from the upstream-side gas supply passage 37, and the gas passing through the upstream-side gas supply passage 37 does not flow to the outside of the holding casing 5 from the opening 86.

As shown in FIG. 3, in the second input mode, the piston portion 32 is rotated relative to the cylinder portion 31 from the first input mode about 90° toward the clockwise direction when seen from the axially parallel outward direction. Thus, in the second input mode, in the first space portion 71A, the inside opening 85 faces the upstream-side gas supply passage 37, and the seal member 88 is disposed at an angular position apart from the upstream-side gas supply passage 37 in the directions around the movement axis. Therefore, in the second input mode, the upstream-side air supply passage 37 is in communication with the first space portion 71A. As a result, in the second input mode, the gas is supplied to the communication passage 78 from the upstream-side gas supply passage 37 through the inside opening 85.

In the second input mode, when the opening 86 of the communication passage 78 is blocked by, for example, a finger of a surgeon, the outflow of the gas passing through the upstream-side gas supply passage 37 to the outside of the holding casing 5 from the opening 86 is prevented. The opening 86 of the communication passage 78 is blocked in the second input mode, so that the pressure in the first space portion 71A is increased by the gas supplied through the upstream-side gas supply passage 37. As a result, the valve member 75 is opened, and the communication between the first space portion 71A and the second space portion 71B is allowed. That is, when the opening 86 of the communication passage 78 is closed in the second input mode, the communication between the first space portion 71A and the second space portion 71B is allowed by the pressure of the gas supplied to the first space portion 71A through the upstream-side gas supply passage 37.

The communication between the first space portion 71A and the second space portion 71B is allowed, so that the gas supplied to the first space portion 71A through the upstream-side air supply passage 37 is supplied to the second space portion 71B. That is, when the opening 86 of the communication passage 78 is blocked in the second input mode, the valve member 75 serves as a first fluid passage open-or-close portion which supplies, to the second space portion 71B, the gas (first fluid) that has been supplied to the first space portion 71A through the upstream-side gas supply passage 37. As a result, the gas is supplied to the downstream-side gas supply passage 35 from the upstream-side gas supply passage 37 through the first space portion 71A and the second space portion 71B. That is, the fluid passages are changed in a region located to a downstream direction side from the hollow portion 58 so that the downstream-side gas supply passage 35 supplies the gas which has passed through the first space portion 71A and the second space portion 71B.

The valve member 75 is a check valve. Thus, even when the first space portion 71A is in communication with the second space portion 71B, the gas flows into the second space portion 71B from the first space portion 71A, but the gas does not flow into the first space portion 71A from the second space portion 71B.

As shown in FIG. 2 and FIG. 3, in the first input mode and the second input mode, the space between the cylinder portion 31 and the piston portion 32 is kept airtight and watertight in the seal member 73 disposed in the third space portion 71C. Thus, in the first input mode and the second input mode, the communication between the upstream-side water supply passage 38 and the downstream-side water supply passage 36 in the third space portion 71C is blocked by the seal member 73. Therefore, in the first input mode and the second input mode, the water is not supplied to the downstream-side water supply passage 36 which is the second downstream-side fluid passage from the upstream-side water supply passage 38 which is the second upstream-side fluid passage.

As shown in FIG. 4, in the third input mode, the piston portion 32 has moved relative to the cylinder portion 31 by a predetermined distance from the first input mode or the second input mode toward the axially parallel inward direction. A cylinder side inclined surface 91 is provided to the cylinder portion 31. A valve side inclined surface 92 having a shape corresponding to the cylinder side inclined surface 91 is provided to the valve member 75.

In the third input mode, the valve side inclined surface 92 is in close contact with the cylinder side inclined surface 91. Thus, in the third input mode, the space between the cylinder portion 31 and the piston portion 32 is kept gastight and liquid-tight in the valve member 75. In the third input mode, the valve member 75 is closed, and the communication between the first space portion 71A and the second space portion 71B is blocked regardless of whether the opening 86 of the communication passage 78 is blocked or not. Therefore, in the third input mode, the gas does not flow into the second space portion 71B from the first space portion 71A. As a result, in the third input mode, the gas is not supplied to the downstream-side gas supply passage 35 which is the first downstream-side fluid passage from the upstream-side gas supply passage 37 which is the first upstream-side fluid passage.

In the third input mode, the seal member 73 disposed in the third space portion 71C does not contact the cylinder portion 31, and the space between the cylinder portion 31 and the piston portion 32 is not kept airtight and watertight in the seal member 73. Thus, in the third input mode, the upstream-side water supply passage 38 is in communication with the downstream-side water supply passage 36 in the third space portion 71C. As a result, in the third input mode, water is supplied to the downstream-side water supply passage 36 which is the second downstream-side fluid passage from the upstream-side water supply passage 38 which is the second upstream-side fluid passage through the third space portion 71C. That is, the fluid passages are changed in a part located to the downstream direction side from the hollow portion 58 so that the downstream-side water supply passage 36 supplies the water which has passed through the third space portion 71C.

Figure 7:
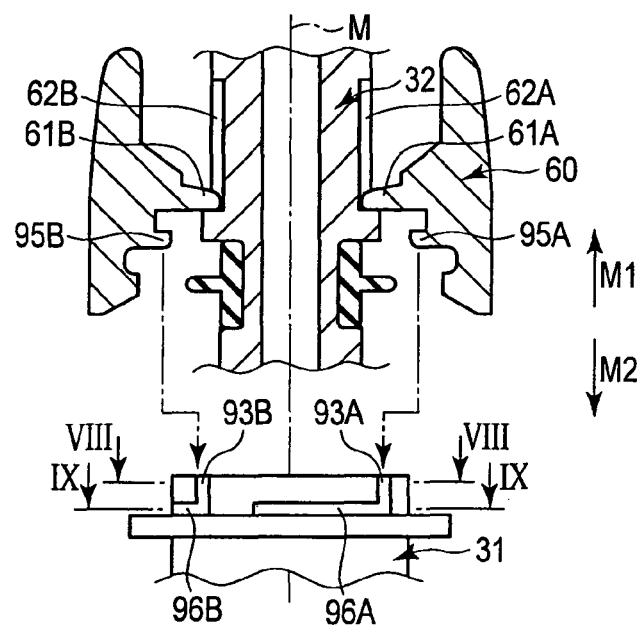
FIG. 7 is a schematic diagram illustrating a configuration which attaches and detaches a connection cap to and from a cylinder portion according to the first embodiment.

FIG. 7 is a diagram illustrating a configuration which attaches and detaches the connection cap 60 to and from the cylinder portion 31. As shown in FIG. 7, the connection cap 60 which is the intermediary member is attached to and detached from the cylinder portion 31 while the piston portion 32 which is the shaft is attached to the connection cap 60. That is, the connection cap 60 and the piston portion 32 are attached to and detached from the cylinder portion 31 together. Thus, the piston portion 32 and the connection cap 60 are attached to and detached from the cylinder portion 31 while the position of the piston portion 32 relative to the connection cap 60 in the directions around the movement axis is set.

Figure 8:
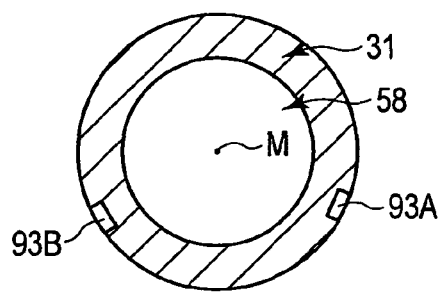
FIG. 8 is a sectional view taken along the line VIII-VIII of FIG. 7.
Figure 9:
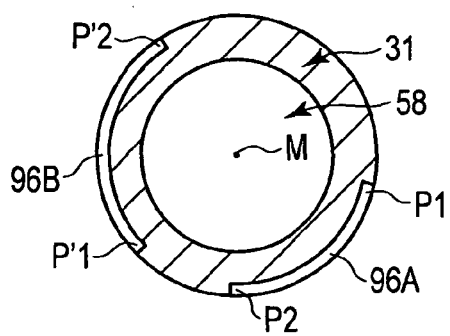
FIG. 9 is a sectional view taken along the line IX-IX of FIG. 7.

FIG. 8 is a sectional view taken along the line VIII-VIII of FIG. 7. FIG. 9 is a sectional view taken along the line IX-IX of FIG. 7. As shown in FIG. 7 and FIG. 8, axially parallel engagement slots (axially parallel engagement portions) 93A and 93B as cylinder side engagement portions extend in the cylinder portion 31 along the movement axis M. The axially parallel engagement slots 93A and 93B are located at angular positions apart from each other in the directions around the movement axis (the circumferential directions of the cylinder portion 31). In the present embodiment, the axially parallel engagement slot 93B is located at an angular position apart from the axially parallel engagement slot 93A by about 120° toward the clockwise direction when seen from the axially parallel outward direction (the direction of an arrow M1 in FIG. 7).

Engagement protrusions 95A and 95B s member side engagement portions are provided in the connection cap 60 which is the intermediary member. The engagement protrusions 95A and 95B are located at angular positions apart from each other in the directions around the movement axis. In the present embodiment, the engagement protrusion 95B is located at an angular position apart from the engagement protrusion 95A by about 120° toward the clockwise direction when seen from the axially parallel outward direction. The engagement protrusion 95A is engageable with the axially parallel engagement slot 93A, and the engagement protrusion 95B is engageable with the axially parallel engagement slot 93B.

When each of the engagement protrusions 95A and 95B moves in the corresponding axially parallel engagement slot 93A or 93B toward the axially parallel inward direction (the direction of an arrow M2 in FIG. 7) while each of the engagement protrusions 95A and 95B is engaged with the corresponding axially parallel engagement slot 93A or 93B, the piston portion 32 and the connection cap 60 are attached to the cylinder portion 31. When each of the engagement protrusions 95A and 95B moves in the corresponding axially parallel engagement slot 93A or 93B toward the axially parallel outward direction while each of the engagement protrusions 95A and 95B is engaged with the corresponding axially parallel engagement slot 93A or 93B, the piston portion 32 and the connection cap 60 are removed from the cylinder portion 31. That is, when each of the engagement protrusions 95A and 95B moves in the corresponding axially parallel engagement slot 93A or 93B along the movement axis M while each of the engagement protrusions 95A and 95B is engaged with the corresponding axially parallel engagement slot 93A or 93B, the piston portion 32 and the connection cap 60 are attached to and detached from the cylinder portion 31 together.

Here, the angular positions of the piston portion 32 and the connection cap 60 relative to the cylinder portion 31 in the directions around the movement axis in the first input mode are reference positions. Each of the engagement protrusions 95A and 95B is located at the angular position to be engageable with the corresponding axially parallel engagement slot 93A or 93B in the directions around the movement axis only when the piston portion 32 and the connection cap 60 are located at the reference positions in the directions around the movement axis. Therefore, the piston portion 32 and the connection cap 60 can be attached to and detached from the cylinder portion 31 only when the piston portion 32 and the connection cap 60 are located at the reference positions which are the angular positions in the first input mode in the directions around the movement axis. That is, the axially parallel engagement slots (cylinder side engagement portions) 93A and 93B and the engagement protrusions (member side engagement portions) 95A and 95B serve as attachment-and-detachment position setting portions which set an attachment-and-detachment position of the piston portion 32 relative to the cylinder portion 31 so that the piston portion 32 can be attached to and detached from the cylinder portion 31 only when the piston portion 32 is located at the reference position in the first input mode relative to the cylinder portion 31 in the directions around the movement axis.

As shown in FIG. 7 and FIG. 9, circumferential direction engagement slots (circumferential direction engagement portions) 96A and 96B as the cylinder side engagement portions extend in the cylinder portion 31 along the directions around the movement axis (the circumferential directions of the cylinder portion 31). The circumferential direction engagement slot 96A is continuous with the axially parallel engagement slot 93A, and is provided over a predetermined angular range from the axially parallel engagement slot 93A in the directions around the movement axis. In the present embodiment, the circumferential direction engagement slot 96A extends over an angular range of about 90° toward the clockwise direction from the axially parallel engagement slot 93A when seen from the axially parallel outward direction. The circumferential direction engagement slot 96B is continuous with the axially parallel engagement slot 93B, and is provided over a predetermined angular range from the axially parallel engagement slot 93B in the directions around the movement axis. In the present embodiment, the circumferential direction engagement slot 96B extends over an angular range of about 90° toward the clockwise direction from the axially parallel engagement slot 93B when seen from the axially parallel outward direction.

When the piston portion 32 and the connection cap 60 are attached to the cylinder portion 31, the engagement protrusion 95A is engaged with the circumferential direction engagement slot 96A, and the engagement protrusion 95B is engaged with the circumferential direction engagement slot 96B. When each of the engagement protrusions 95A and 95B moves in the corresponding circumferential direction engagement slot 96A or 96B in the directions around the movement axis while each of the engagement protrusions 95A and 95B is engaged with the corresponding circumferential direction engagement slot 96A or 96B, the piston portion 32 and the connection cap 60 rotate together relative to the cylinder portion 31 around the movement axis M.

The engagement protrusion 95A is only movable in the circumferential direction engagement slot 96A in a movement range between a first engagement position P1 and a second engagement position P2. That is, the engagement protrusion 95A is only engageable with the circumferential direction engagement slot 96A in the movement range between the first engagement position P1 and the second engagement position P2. Here, the first engagement position P1 is located at a counterclockwise direction side end of the circumferential direction engagement slot 96A when seen from the axially parallel outward direction, and the second engagement position P2 is located at a clockwise direction side end of the circumferential direction engagement slot 96A when seen from the axially parallel outward direction. The engagement protrusion 95B is only movable in the circumferential direction engagement slot 96B in a movement range between a first engagement position P'1 and a second engagement position P'2. That is, the engagement protrusion 95B is only engageable with the circumferential direction engagement slot 96B in the movement range between the first engagement position P'1 and the second engagement position P'2. Here, the first engagement position P'1 is located at a counterclockwise direction side end of the circumferential direction engagement slot 96B when seen from the axially parallel outward direction, and the second engagement position P'2 is located at a clockwise direction side end of the circumferential direction engagement slot 96B when seen from the axially parallel outward direction.

When the engagement protrusion 95A is located at the first engagement position P1, the engagement protrusion 95B is located at the first engagement position P'1. When the engagement protrusion 95A is located at the second engagement position P2, the engagement protrusion 95B is located at the second engagement position P'2. When the engagement protrusion 95A is located at the first engagement position P1 and the engagement protrusion 95B is located at the first engagement position P'1, the piston portion 32 and the connection cap 60 are located at the reference positions which are the angular positions in the first input mode in the directions around the movement axis. The angular positions of the piston portion 32 and the connection cap 60 relative to the cylinder portion 31 in the directions around the movement axis in the second input mode are maximum rotation positions. That is, maximum angular positions are positions at which the piston portion 32 and the connection cap 60 have been rotated relative to the cylinder portion 31 from the reference positions by a predetermined rotation angle in one of the directions around the movement axis. When the engagement protrusion 95A is located at the second engagement position P2 and the engagement protrusion 95B is located at the second engagement position P'2, the piston portion 32 and the connection cap 60 are located at the maximum rotation positions which are the angular positions in the second input mode in the directions around the movement axis.

As described above, the engagement protrusion 95A is only engageable with the circumferential direction engagement slot 96A in the movement range between the first engagement position P1 and the second engagement position P2, and the engagement protrusion 95B is only engageable with the circumferential direction engagement slot 96B in the movement range between the first engagement position P'1 and the second engagement position P'2. Thus, the piston portion 32 and the connection cap 60 are rotatable relative to the cylinder portion 31 in the directions around the movement axis between the reference positions which are the angular positions in the first input mode and the maximum rotation positions which are the angular positions in the second input mode. Thus, the rotation range of the piston portion 32 is regulated between the reference position and the maximum rotation position. That is, the circumferential direction engagement slots (circumferential direction engagement portions) 96A and 96B and the engagement protrusions (member side engagement portions) 95A and 95B serve as rotation range regulating portions which are configured to regulate the rotation range of the piston portion 32 so that the piston portion 32 which is the shaft rotates relative to the cylinder portion 31 in the directions around the movement axis between the reference position and the maximum rotation position.

Now, the functions and advantageous effects of the endoscopic fluid passage changeover valve unit 30 and the endoscope 1 are described. When a gas or water is supplied to the distal portion of the insertion section 2 of the endoscope 1, the gas is supplied from the air supply source 42 through the air supply tube 41 and the upstream-side gas supply passage 37. The water is supplied from the water supply source 50 through the water supply tube 46 and the upstream-side water supply passage 38.

When the rotation operation and the movement operation are not performed in the operation input button 65, the first input mode is set. In the first input mode, the communication between the upstream-side gas supply passage 37 and the first space portion 71A is blocked by the seal member 88. Therefore, in the first input mode, the gas does not flow into the first space portion 71A from the upstream-side gas supply passage 37, and the gas is not supplied to the downstream-side gas supply passage 35 from the upstream air supply passage 37. In the first input mode, the gas is not supplied to the communication passage 78 from the upstream-side gas supply passage 37, and the gas (carbon dioxide) passing through the upstream-side gas supply passage 37 does not flow to the outside of the holding casing 5 from the opening 86.

In the first input mode, the communication between the upstream-side water supply passage 38 and the downstream-side water supply passage 36 in the third space portion 71C is blocked by the seal member 73. Thus, in the first input mode, water is not supplied to the downstream-side water supply passage 36 which is the second downstream-side fluid passage from the upstream-side water supply passage 38 which is the second upstream-side fluid passage. As described above, in the first input mode, the gas and water are not supplied to the distal portion (junction flow passage 53) of the insertion section 2.

When the piston portion 32 is rotated the predetermined rotation angle around the movement axis M from the first input mode by the rotation operation in the operation input button 65, the piston portion 32 is set in the second input mode. In the second input mode, the upstream-side gas supply passage 37 is in communication with the first space portion 71A. Thus, in the second input mode, the gas is supplied to the communication passage 78 from the upstream-side gas supply passage 37 through the inside opening 85. In the second input mode, when the opening 86 of the communication passage 78 is blocked by, for example, the finger of the surgeon, the outflow of the gas passing through the upstream-side gas supply passage 37 to the outside of the holding casing 5 from the opening 86 is prevented. The opening 86 of the communication passage 78 is closed in the second input mode, so that the communication between the first space portion 71A and the second space portion 71B is allowed by the pressure of the gas supplied to the first space portion 71A through the upstream-side gas supply passage 37. When the communication between the first space portion 71A and the second space portion 71B is allowed, the gas supplied to the first space portion 71A through the upstream-side gas supply passage 37 is supplied to the second space portion 71B. As a result, the gas is supplied to the downstream-side gas supply passage 35 from the upstream-side gas supply passage 37 through the first space portion 71A and the second space portion 71B.

In the second input mode, the communication between the upstream-side water supply passage 38 and the downstream-side water supply passage 36 in the third space portion 71C is blocked by the seal member 73. Thus, in the second input mode, water is not supplied to the downstream-side water supply passage 36 which is the second downstream-side fluid passage from the upstream-side water supply passage 38 which is the second upstream-side fluid passage. As described above, in the second input mode, the gas is supplied to the distal portion (junction flow passage 53) of the insertion section 2 when the opening 86 of the communication passage 78 is blocked. That is, when the opening 86 of the communication passage 78 is closed, the fluid passages are changed in the part located to the downstream direction side from the hollow portion 58 so that the downstream-side gas supply passage 35 supplies the gas which has passed through the first space portion 71A and the second space portion 71B. In this case, water is not supplied to the distal portion (junction flow passage 53) of the insertion section 2.

When the piston portion 32 is moved a predetermined distance (along the movement axis M) from the first input mode or the second input mode toward the axially parallel inward direction by the movement operation in the operation input button 65, the piston portion 32 is set in the third input mode. In the third input mode, regardless of whether the opening 86 of the communication passage 78 is blocked or not, the valve member 75 is closed, and the communication between the first space portion 71A and the second space portion 71B is blocked. Therefore, in the third input mode, the gas does not flow into the second space portion 71B from the first space portion 71A. As a result, in the third input mode, the gas is not supplied to the downstream-side gas supply passage 35 which is the first downstream-side fluid passage from the upstream-side gas supply passage 37 which is the first upstream-side fluid passage.

In the third input mode, the upstream-side water supply passage 38 is in communication with the downstream-side water supply passage 36 in the third space portion 71C. As a result, in the third input mode, the water is supplied to the downstream-side water supply passage 36 which is the second downstream-side fluid passage from the upstream-side water supply passage 38 which is the second upstream-side fluid passage through the third space portion 71C. As described above, in the third input mode, the water is supplied to the distal portion (junction flow passage 53) of the insertion section 2. That is, the fluid passages are changed in the part located to the downstream direction side from the hollow portion 58 so that the downstream-side water supply passage 36 supplies the water which has passed through the third space portion 71C. In this case, the gas is not supplied to the distal portion (junction flow passage 53) of the insertion section 2.

As described above, in the first input mode, the communication between the upstream-side gas supply passage 37 and the first space portion 71A is blocked by the seal member 88, so that the gas (carbon dioxide) passing through the upstream-side gas supply passage 37 does not flow to the outside of the holding casing 5 from the opening 86. In the second input mode in which the rotation operation is performed in the operation input button 65 and in the third input mode in which the movement operation is performed in the operation input button 65, the opening 86 of the communication passage 78 is blocked by the finger of the surgeon. Thus, in the second input mode and the third input mode, the outflow of the gas (carbon dioxide) passing through the upstream-side gas supply passage 37 to the outside of the holding casing 5 from the opening 86 is effectively prevented. Therefore, in the endoscopic fluid passage changeover valve unit 30, even when carbon dioxide is supplied as a gas to the distal portion of the insertion section 2, the outflow of carbon dioxide to the outside of the holding casing 5 (examination room) from the opening 86 of the communication passage 78 can be effectively prevented.

In the endoscopic fluid passage switching valve unit 30, when the piston portion 32 is rotated the predetermined rotation angle around the movement axis M from the first input mode, the piston portion 32 is set in the second input mode. When the piston portion 32 is moved a predetermined distance along the movement axis M from the first input mode or the second input mode, the piston portion 32 is set in the third input mode. That is, the direction toward which the piston portion 32 is moved differs between the rotation operation of changing to the second mode in which the gas is supplied to the downstream-side gas supply passage 35 and the movement operation of changing to the third mode in which water is supplied to the downstream-side water supply passage 36. Therefore, the surgeon can easily perform the operation of changing, in the region located to the downstream direction side from the hollow portion 58, the fluid passages to supply the fluid (gas or water) which has passed through the hollow portion 58.

In the endoscopic fluid passage changeover valve unit 30, the piston portion 32 and the connection cap 60 can be attached to and detached from the cylinder portion 31 only when the piston portion 32 and the connection cap 60 are located at the reference positions which are the angular positions in the first input mode in the directions around the movement axis. Thus, the surgeon recognizes that the angular position at which the piston portion 32 and the connection cap 60 are attached to and detached from the cylinder portion 31 is the angular position (reference position) of the piston portion 32 in the first input mode. Therefore, the surgeon can easily recognize the reference position which is the angular position of the piston portion 32 in the first input mode in the directions around the movement axis. Consequently, the surgeon can easily perform the rotation operation in the operation input button 65.

Furthermore, in the endoscopic fluid passage changeover valve unit 30, the piston portion 32 and the connection cap 60 are rotatable relative to the cylinder portion 31 in the directions around the movement axis between the reference positions which are the angular positions in the first input mode and the maximum rotation positions which are the angular positions in the second input mode. Thus, the rotation range of the piston portion 32 is regulated between the reference position and the maximum rotation position. Since the rotation range of the piston portion 32 is regulated between the reference position in the first input mode and the maximum rotation position in the second input mode, the surgeon can easily switch between the first input mode and the second input mode. That is, the surgeon can easily perform the rotation operation in the operation input button 65.

Second Embodiment

Now, a second embodiment of the present invention is described with reference to FIG. 10 to FIG. 13. The second embodiment is the following modification of the configuration according to the first embodiment. The same parts as those according to the first embodiment are indicated by the same reference signs, and are not described.

Figure 10:
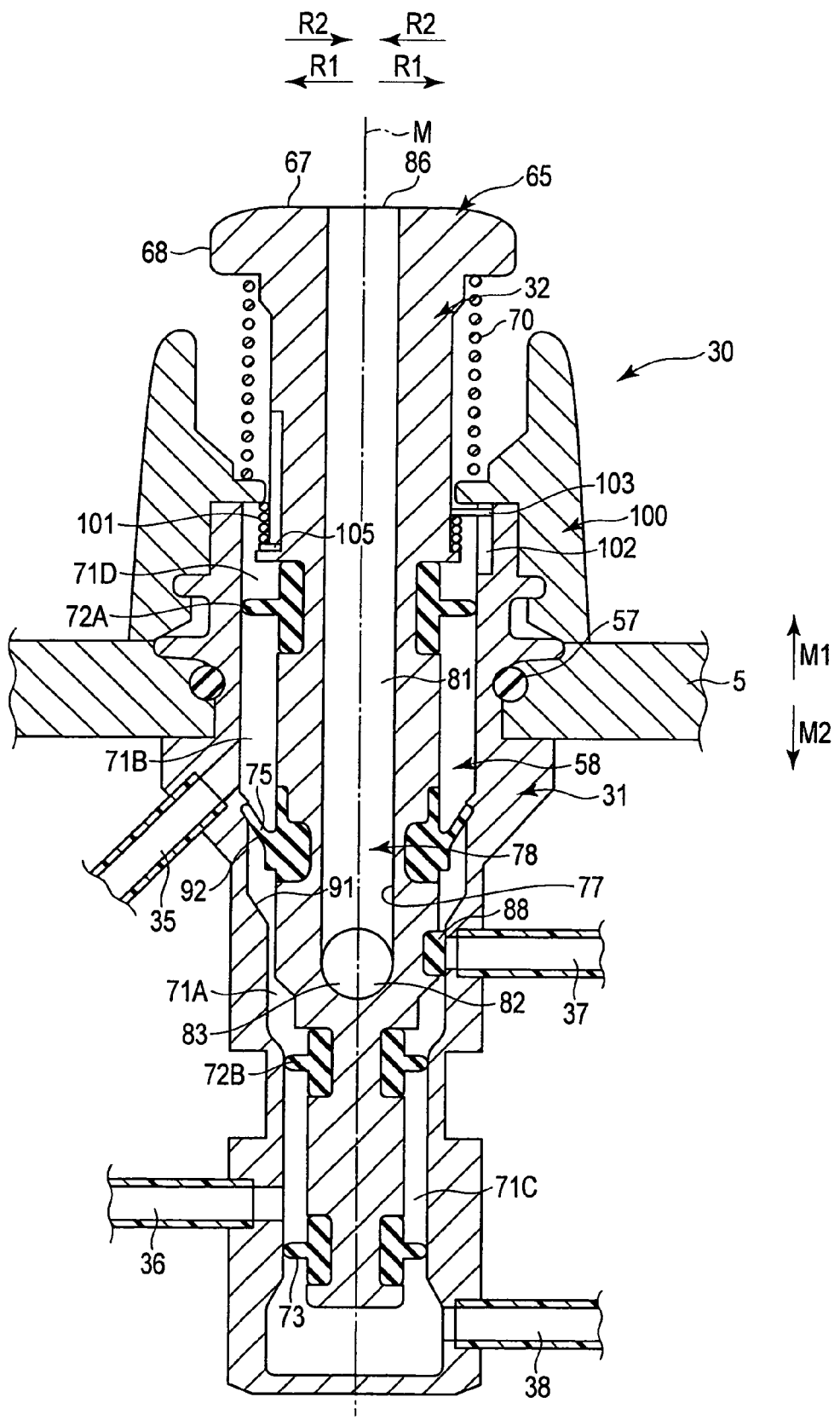
FIG. 10 is a sectional view schematically showing the configuration of an endoscopic fluid passage changeover valve unit in a first input mode according to a second embodiment.
Figure 11:
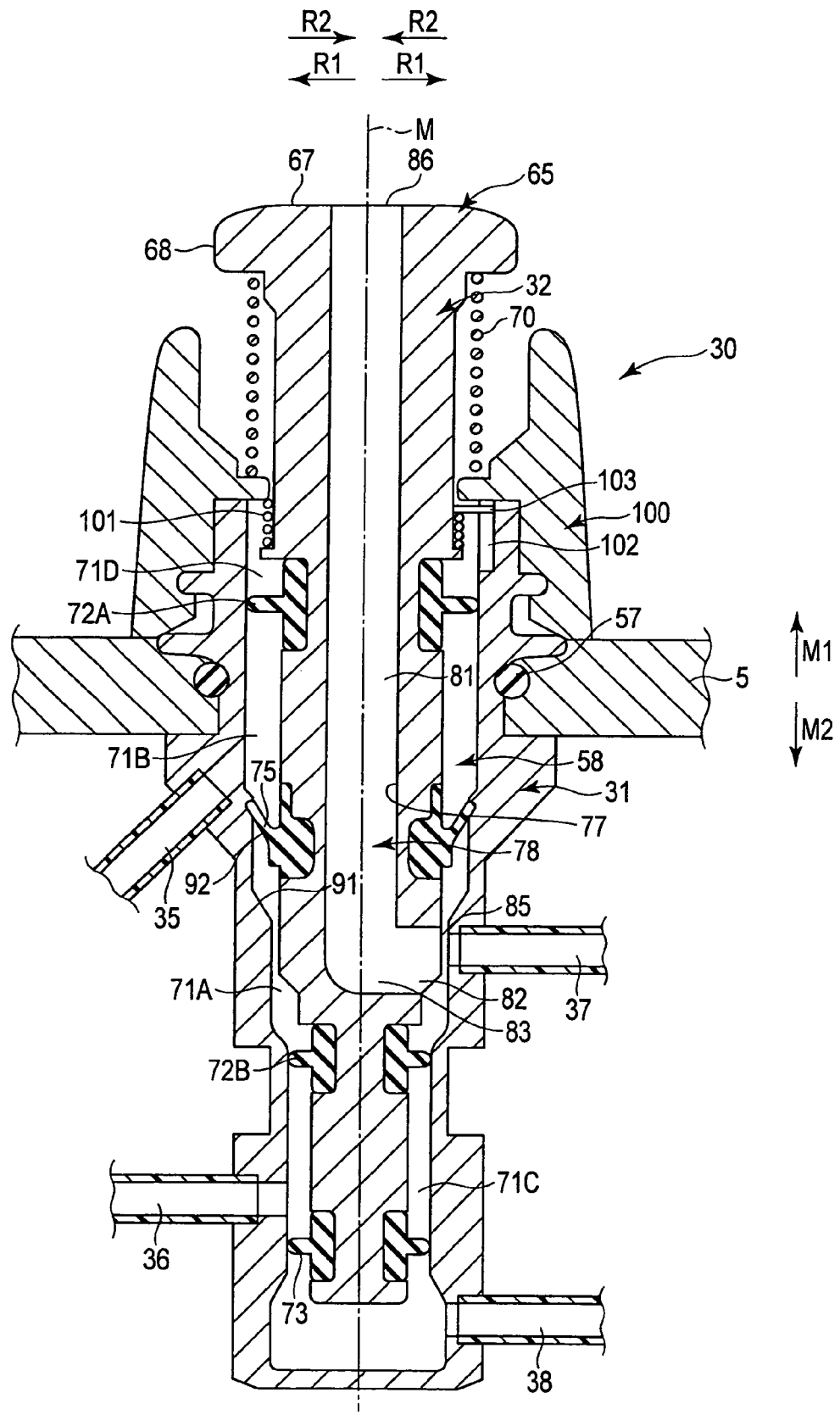
FIG. 11 is a sectional view schematically showing the configuration of the endoscopic fluid passage changeover valve unit in a second input mode according to the second embodiment.
Figure 12:
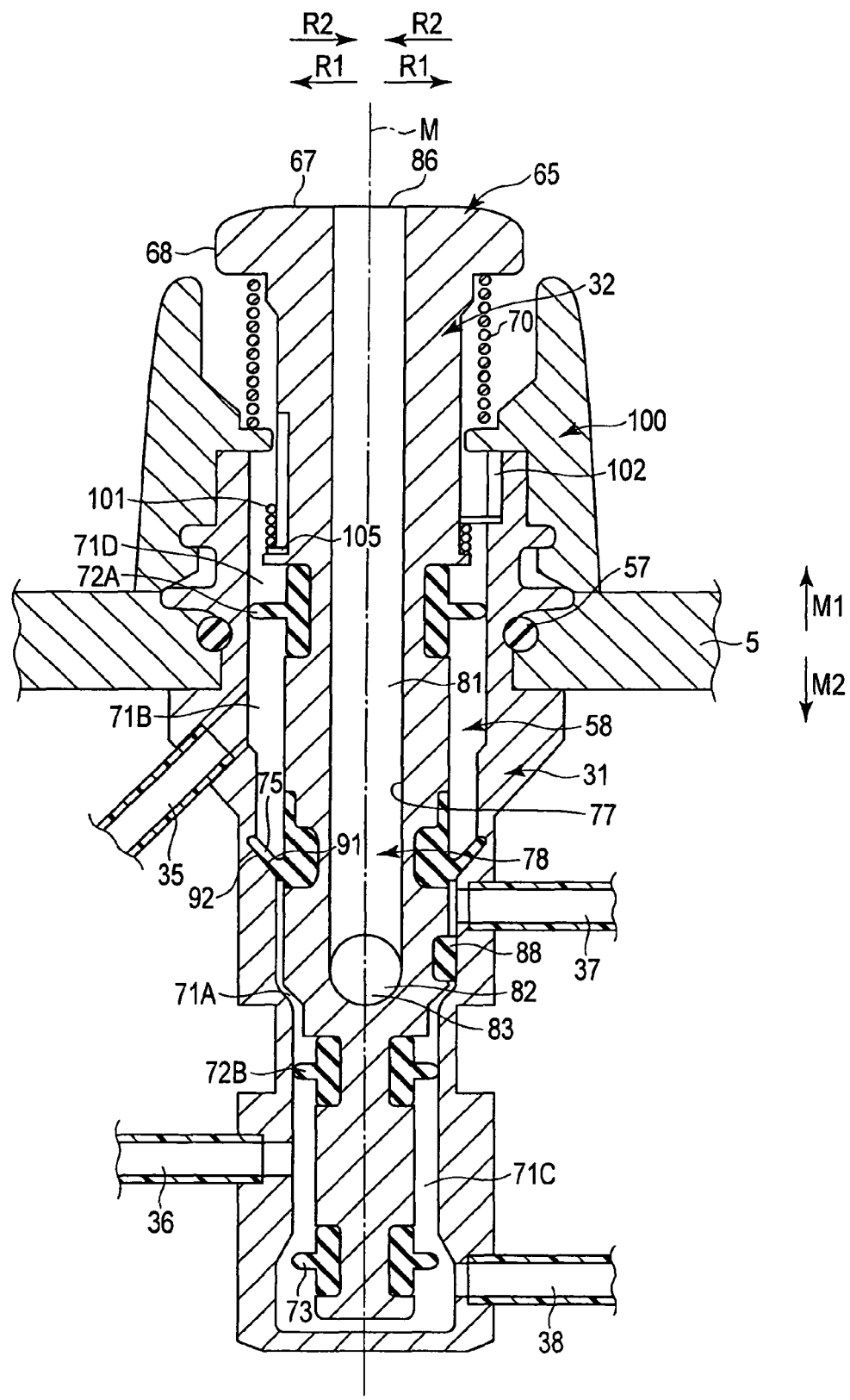
FIG. 12 is a sectional view schematically showing the configuration of the endoscopic fluid passage changeover valve unit in a third input mode according to the second embodiment.

FIG. 10 to FIG. 12 are diagrams showing the endoscopic fluid passage changeover valve unit 30 according to the present embodiment. Here, FIG. 10 shows a first input mode in which the rotation operation and the movement operation are not input in the operation input button 65. FIG. 11 shows a second input mode in which the piston portion 32 has been rotated a predetermined rotation angle around the movement axis M from the first input mode by the rotation operation in the operation input button 65. In the present embodiment, the piston portion 32 is rotated relative to the cylinder portion 31 from the first input mode by about 90° toward the clockwise direction when seen from the axially parallel outward direction, and the piston portion 32 is thereby set in the second input mode. Moreover, FIG. 12 shows a third input mode in which the piston portion 32 has moved a predetermined distance along the movement axis M from the first input mode by the movement operation in the operation input button 65. In the present embodiment, the piston portion 32 is moved relative to the cylinder portion 31 toward the axially parallel inward direction from the first input mode, and is thereby set in the third input mode.

As shown in FIG. 10 to FIG. 12, in the present embodiment, a connection cap 100 is provided instead of the connection cap 60 according to the first embodiment. The connection cap 100 is fixed to the cylinder portion 31. In the present embodiment, the piston portion 32 is rotatable relative to the cylinder portion 31 and the connection cap 100 around the movement axis M. Therefore, in contrast to the connection cap 60 according to the first embodiment, the connection cap 100 does not rotate together with the piston portion 32. However, in the same manner as the connection cap 60, the connection cap 100 is attached to and detached from the cylinder portion 31 together with the piston portion 32. In the present embodiment, one end of the return spring 70 is connected to the operation input button 65 of the piston portion 32 and the other end is connected to the connection cap 100.

In the present embodiment, a torsional spring 101 is provided. The torsional spring 101 is located between the cylinder portion 31 and the piston portion 32 in the cylinder diametrical directions, and located in the fourth space portion 71D. When the piston portion 32 is attached to the cylinder portion 31, the cylinder portion 31 is connected to the piston portion 32 via the torsional spring 101.

When the piston portion 32 is located at the reference position which is the angular position in the first input mode, an urging force is not applied to the piston portion 32 from the torsional spring 101. When the piston portion 32 attached to the cylinder portion 31 rotates relative to the cylinder portion 31 in one of the directions around the movement axis M from the reference position, the urging force to return the piston portion 32 to the reference position is applied from the torsional spring 101. That is, when the piston portion 32 rotates from the reference position toward the maximum rotation position which is the angular position in the second input mode, the urging force is applied to the piston portion 32 toward the reference position. The torsional spring 101 is provided so that the piston portion 32 is located at the reference position which is the angular position in the first input mode in the directions around the movement axis when the rotation operation is not performed in the operation input button 65.

FIG. 13 is a diagram showing a configuration in which the cylinder portion 31 and the piston portion 32 are connected by the torsional spring 101. As shown in FIG. 10 to FIG. 13, an engagement slot 102 as a cylinder side engagement portion extends along the movement axis M in the cylinder portion 31. At one end of the torsional spring 101, an engagement protrusion 103 is provided as a spring side engagement portion which is engageable with the engagement slot 102. A piston fixing portion 105 fixed to the piston portion 32 is provided at the other end of the torsional spring 101. When the engagement protrusion 103 moves in the engagement slot 102 along the movement axis M while the engagement protrusion 103 of the torsional spring 101 attached to the piston portion 32 is engaged with the engagement slot 102 of the cylinder portion 31, the piston portion 32 is attached to and detached from the cylinder portion 31. In this case, the urging force is not applied to the piston portion 32 from the torsional spring 101.

The engagement protrusion 103 is located at an angular position to be engageable with the engagement slot 102 in the directions around the movement axis only when the piston portion 32 to which the urging force is not applied from the torsional spring 101 is located at the reference position in the directions around the movement axis. Therefore, the piston portion 32 and the torsional spring 101 can be attached to and detached from the cylinder portion 31 only when the piston portion 32 is located at the reference position which is the angular position in the first input mode in the directions around the movement axis. That is, the engagement slot (cylinder side engagement portion) 102 and the engagement protrusion (spring side engagement portion) 103 serve as attachment-and-detachment position setting portions which are configured to set an attachment-and-detachment position of the piston portion 32 relative to the cylinder portion 31 so that the piston portion 32 can be attached to and detached from the cylinder portion 31 only when the piston portion 32 is located at the reference position in the first input mode relative to the cylinder portion 31 in the directions around the movement axis.

When the piston portion 32 has been rotated to the maximum rotation position which is the angular position in the second input mode, the piston portion 32 does not rotate toward a direction departing from the reference position due to the urging force from the return spring 70. That is, the torsional spring 101 applies the urging force to the piston portion 32 so that the piston portion 32 does not rotate from the maximum rotation position toward the direction away from the reference position. For example, the elastic constant, the material, and the number of turns of the torsional spring 101 are adjusted so that the piston portion 32 does not rotate from the maximum rotation position toward the direction departing from the reference position.

As described above, the torsional spring 101 is provided so that the piston portion 32 is rotatable relative to the cylinder between the reference position which is the angular position in the first input mode and the maximum rotation position which is the angular position in the second input mode. Thus, the rotation range of the piston portion 32 is regulated between the reference position and the maximum rotation position. That is, the torsional spring 101 serves as a rotation range regulating portion which is configured to regulate the rotation range of the piston portion 32 so that the piston portion 32 which is the shaft rotates relative to the cylinder portion 31 in the directions around the movement axis between the reference position and the maximum rotation position.

The present embodiment also has the functions and advantageous effects similar to those according to the first embodiment. That is, even when carbon dioxide is supplied as a gas to the distal portion of the insertion section 2, the outflow of carbon dioxide to the outside of the holding casing 5 (examination room) from the opening 86 of the communication passage 78 can be effectively prevented. The direction toward which the piston portion 32 is moved differs between the rotation operation of changing to the second mode in which the gas is supplied to the downstream-side gas supply passage 35 and the movement operation of changing to the third mode in which water is supplied to the downstream-side water supply passage 36. Therefore, the surgeon can easily perform the operation of changing, in the region located to the downstream direction side with respect to the hollow portion 58, the fluid passages to supply the fluid (gas or water) which has passed through the hollow portion 58. The surgeon can easily recognize the reference position which is the angular position of the piston portion 32 in the first input mode in the directions around the movement axis. Moreover, since the rotation range of the piston portion 32 is regulated between the reference position in the first input mode and the maximum rotation position in the second input mode, the surgeon can easily switch between the first input mode and the second input mode.

Third Embodiment

Now, a third embodiment of the present invention is described with reference to FIG. 14 and FIG. 15. The third embodiment is the following modification of the configuration according to the first embodiment. The same parts as those according to the first embodiment are indicated by the same reference signs, and are not described.

FIG. 14 and FIG. 15 are diagrams showing the configuration of the operation input button 65 of the piston portion 32. FIG. 14 is a diagram showing the operation input button 65 as seen from the axially parallel outward direction. FIG. 15 is a diagram showing the operation input button 65 as seen from one direction among the diametrically outer peripheral direction. As shown in FIG. 14 and FIG. 15, the operation input button 65 includes the first exposed surface 67 facing in the axially parallel outward direction, and the second exposed surface 68 facing in the diametrically outer peripheral direction, as in the first embodiment. In the present embodiment, the operation input button 65 also includes an input main body 107, and an input projection 108 projecting from the input main body 107 toward the diametrically outer peripheral direction (the direction departing from the movement axis M in the plane perpendicular to the movement axis M).

The input main body 107 is formed into a circle around the movement axis M when seen from the axially parallel outward direction. That is, the input main body 107 is formed point-symmetrically with respect to the movement axis M when seen from the axially parallel outward direction. In the operation input button 65, the input projection 108 projects toward the diametrically outer peripheral direction from the input main body 107 which is point-symmetrical with respect to the movement axis M. The input projection 108 is provided so that the operation input button 65 has a shape which is point-asymmetrical with respect to the movement axis M when seen from the axially parallel outward direction.

In the present embodiment, a bending part 110 in which the communication passage 78 bends is provided inside the operation input button 65. In the present embodiment, the communication passage 78 includes a diametrical direction passage portion 111 extending from the bending part 110 (the movement axis M) along the cylinder diametrical directions. In the communication passage 78, the bending part 110 is located between the axially parallel passage portion 81 and the diametrical direction passage portion 111. The diametrical direction passage portion 111 extends from the movement axis M toward the input projection 108. In the present embodiment, the opening 86 of the communication passage 78 is not located on the first exposed surface 67. That is, the opening 86 of the communication passage 78 is provided in the diametrical direction passage portion 111. The opening 86 of the communication passage 78 is opened with respect to the outside of the holding casing 5 on the second exposed surface 68 in the input projection 108.

The present embodiment also has the following functions and advantageous effects in addition to the functions and advantageous effects similar to those according to the first embodiment. In the operation input button 65 of the endoscopic fluid passage changeover valve unit 30 according to the present embodiment, the input projection 108 projects toward the diametrically outer peripheral direction from the input main body 107 which is point-symmetrical with respect to the movement axis M. The input projection 108 is provided in the operation input button 65 so that the surgeon can easily rotate the piston portion 32 around the movement axis M. That is, the surgeon can more easily perform the rotation operation in the operation input button 65.

The opening 86 of the communication passage 78 is opened to the outside of the holding casing 5 on the second exposed surface 68 in the input projection 108. The opening 86 is provided on the second exposed surface 68 in the input projection 108 so that the surgeon can easily block the opening 86 of the communication passage 78 with the finger in the rotation operation and the movement operation in the operation input button 65 including the input projection 108.

Modification of Third Embodiment

As in a modification of the third embodiment shown in FIG. 16, the input projection 108 may be located at an angular position different from that in the third embodiment in the directions around the movement axis. In the present modification, the input projection 108 is located at an angular position about 45° apart from that in the third embodiment toward the clockwise direction when seen from the axially parallel outward direction. In the present modification as well, the input projection 108 projects from the input main body 107 toward the diametrically outer peripheral direction (the direction departing from the movement axis M in the plane perpendicular to the movement axis M). The input projection 108 is provided so that the operation input button 65 has a shape which is point-asymmetrical with respect to the movement axis M when seen from the axially parallel outward direction.

Other Modifications

According to the embodiments and modification described above, in the endoscopic fluid passage changeover valve unit 30, the seal member 88 has only to be provided between the cylinder portion 31 and the piston portion 32 in the cylinder diametrical directions while the seal member 88 is rotatable relative to the cylinder portion 31 together with the piston portion (shaft) 32. The communication between the upstream-side gas supply passage (first upstream-side fluid passage) 37 and the first space portion 71A has only to be blocked by the seal member 88 in the first input mode, and the communication between the upstream-side gas supply passage 37 and the first space portion 71A has only to be allowed in the second input mode in which the piston portion 72 has been rotated the predetermined rotation angle around the movement axis M from the first input mode. The valve member (first fluid passage open-or-close portion) 75 has only to be provided between the first space portion 71A and the second space portion 71B. The gas (first fluid) supplied to the first space portion 71A through the upstream-side gas supply passage (first upstream-side fluid passage) 37 has only to be supplied to the second space portion 71B by the valve member 75 when the opening 86 of the communication passage 78 is blocked in the second input mode.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscopic fluid passage changeover valve unit comprising:
   a cylinder portion having a hollow portion formed therein;
   a first upstream-side fluid passage that has a downstream end thereof located on an inner peripheral surface of the cylinder portion, and that is configured to supply a first fluid to the hollow portion from the downstream end;
   a shaft that extends along a movement axis to be inserted into the hollow portion, and inside of which a communication passage is formed, the communication passage being opened to an outside of the cylinder portion through an opening and being also opened to the hollow portion in an inside opening located on an outer peripheral surface of the shaft;
   a first seal member that is provided on the outer peripheral surface of the shaft rotatably around the movement axis, and that is located at an angular position apart from the inside opening in circumferential directions of the cylinder portion;
   a connection cap that attaches the shaft to the cylinder portion so that the shaft and the first seal member are rotatable relative to the cylinder portion around the movement axis toward a position where the downstream end of the first upstream-side fluid passage is blocked by the first seal member and toward a position where the inside opening of the communication passage faces the downstream end of the first upstream-side fluid passage; and
   a second seal member that is provided on the outer peripheral surface of the shaft moveably and rotatably with respect to the cylinder portion and that is configured to keep airtight and watertight between the cylinder portion and the shaft.

2. The endoscopic fluid passage changeover valve unit according to claim 1, wherein
   the second seal member includes multiple second seal members,
   the second seal members form space portions between the cylinder portion and the shaft in the hollow portion,
   the shaft is configured to rotate a predetermined rotation angle together with the first seal member around the movement axis from a first input mode in which the first seal member is located at a position to block the downstream end of the first upstream-side fluid passage, and thereby the shaft is configured to be set in a second input mode in which the first seal member is located at a position where the first seal member does not block the downstream end of the first upstream-side fluid passage, and
   the first upstream-side fluid passage is configured to allow the downstream end to be in communication with a first space portion which is one of the space portions in the second input mode of the shaft.

3. The endoscopic fluid passage changeover valve unit according to claim 2, wherein
   the space portions includes a second space portion configured to be allowed to be in communication with the first space portion, and
   the endoscopic fluid passage changeover valve unit includes a first downstream-side fluid passage to which the first fluid that has passed through the first space portion and the second space portion is supplied from the downstream end of the first upstream-side fluid passage.

4. The endoscopic fluid passage changeover valve unit according to claim 3, further comprising a first fluid passage open-or-close portion which is provided between the first space portion and the second space portion in the hollow portion, and which is configured to supply, to the second space portion, the first fluid that has been supplied to the first space portion through the first upstream-side fluid passage when the opening of the communication passage is blocked in the second input mode of the shaft.

5. The endoscopic fluid passage changeover valve unit according to claim 4, wherein
   the space portions includes a third space portion in which communication with the first space portion and the second space portion is blocked, and
   the endoscopic fluid passage changeover valve unit further includes
     a second upstream-side fluid passage which has a downstream end thereof in communication with the third space portion, and which is configured to supply a second fluid different from the first fluid to the third space portion, and
     a second downstream-side fluid passage which has an upstream end thereof in communication with the third space portion, and to which the second fluid that has passed through the third space portion is supplied from the downstream end of the second upstream-side fluid passage.

6. The endoscopic fluid passage changeover valve unit according to claim 5, wherein
   the shaft and the first seal member are movable together relative to the cylinder portion along the movement axis,
   the shaft is configured to move a predetermined distance together with the first seal member along the movement axis from the first input mode or the second input mode, and thereby configured to be set in a third input mode, and
   the endoscopic fluid passage changeover valve unit further includes a second fluid passage open-or-close portion, the second fluid passage open-or-close portion being configured to block the communication between the second upstream-side fluid passage and the second downstream-side fluid passage in the third space portion in the first input mode and the second input mode of the shaft, the second fluid passage open-or-close portion being configured to allow the communication between the second upstream-side fluid passage and the second downstream-side fluid passage in the third space portion in the third input mode.

7. The endoscopic fluid passage changeover valve unit according to claim 6, wherein the first fluid passage open-or-close portion is configured to block the communication between the first space portion and the second space portion in the third input mode regardless of whether the opening of the communication passage is blocked or not.

8. The endoscopic fluid passage changeover valve unit according to claim 4, wherein the first fluid passage open-or-close portion includes a valve member which is configured to allow the communication between the first space portion and the second space portion by pressure of the first fluid that has been supplied to the first space portion through the first upstream-side fluid passage when the opening of the communication passage is blocked in the second input mode.

9. The endoscopic fluid passage changeover valve unit according to claim 2, further comprising an attachment-and-detachment position setting portion which is configured to set an attachment-and-detachment position of the shaft relative to the cylinder portion so that the shaft is allowed to be attached to and detached from the cylinder portion only when the shaft is located at a reference position in the first input mode relative to the cylinder portion in the circumferential directions of the cylinder portion.

10. The endoscopic fluid passage changeover valve unit according to claim 9, further comprising an intermediary member which is rotatable relative to the cylinder portion together with the shaft around the movement axis, wherein the attachment-and-detachment position setting portion includes
a cylinder side engagement portion extending in the cylinder portion along the movement axis, and
a member side engagement portion which is provided in the intermediary member, and which is configured to move in the cylinder side engagement portion along the movement axis while being engaged with the cylinder side engagement portion and thereby configured to attach and detach the shaft and the intermediary member to and from the cylinder portion together.

11. The endoscopic fluid passage changeover valve unit according to claim 10, wherein the member side engagement portion is configured to be located at an angular position to be engageable with the cylinder side engagement portion in the circumferential directions of the cylinder portion only when the shaft is located at the reference position relative to the cylinder portion.

12. The endoscopic fluid passage changeover valve unit according to claim 9, further comprising a torsional spring which connects the cylinder portion to the shaft when the shaft is attached to the cylinder portion, and which is configured to apply an urging force to the shaft to return the shaft to the reference position in accordance with the rotation of the shaft from the reference position relative to the cylinder portion while the shaft is attached to the cylinder portion.

13. The endoscopic fluid passage changeover valve unit according to claim 12, wherein the attachment-and-detachment position setting portion includes
a cylinder side engagement portion extending in the cylinder portion along the movement axis, and
a spring side engagement portion which is provided at one end of the torsional spring, and which is configured to move the cylinder side engagement portion along the movement axis while being engaged with the cylinder side engagement portion and thereby configured to attach and detaches, to and from the cylinder portion, the shaft to which the urging force is not applied from the torsional spring, the spring side engagement portion being configured to be located at an angular position to be engageable with the cylinder side engagement portion in the circumferential directions of the cylinder portion only when the shaft to which the urging force is not applied from the torsional spring is located at the reference position relative to the cylinder portion.

14. The endoscopic fluid passage changeover valve unit according to claim 2, further comprising a rotation range regulating portion which is configured to regulate the rotation range of the shaft so that the shaft rotates relative to the cylinder portion in the circumferential directions of the cylinder portion between a reference position in the first input mode and a maximum rotation position in the second input mode which has been rotated the predetermined rotation angle from the reference position.

15. The endoscopic fluid passage changeover valve unit according to claim 14, further comprising an intermediary member which is rotatable relative to the cylinder portion together with the shaft around the movement axis, wherein the rotation range regulating portion includes
a cylinder side engagement portion extending along the circumferential directions of the cylinder portion, and
a member side engagement portion which is provided in the intermediary member, and which is configured to move in the cylinder side engagement portion along the circumferential directions of the cylinder portion while being engaged with the cylinder side engagement portion so that the shaft and the intermediary member rotate together relative to the cylinder portion around the movement axis.

16. The endoscopic fluid passage changeover valve unit according to claim 15, wherein the member side engagement portion is configured to engage with the cylinder side engagement portion in only a movement range between a first engagement position where the shaft is located at the reference position and a second engagement position where the shaft is located at the maximum rotation position in the circumferential directions of the cylinder portion.

17. The endoscopic fluid passage changeover valve unit according to claim 14, wherein the rotation range regulating portion includes a torsional spring which connects the cylinder portion to the shaft when the shaft is attached to the cylinder portion, and which is configured to apply an urging force to the shaft to return the shaft to the reference position in accordance with the rotation of the shaft from the reference position relative to the cylinder portion while the shaft is attached to the cylinder portion, the torsional spring being configured to apply the urging force to the shaft so that the shaft does not rotate from the maximum rotation position toward a direction departing from the reference position.

18. The endoscopic fluid passage changeover valve unit according to claim 1, wherein
the shaft and the first seal member are movable together relative to the cylinder portion along the movement axis,
the shaft includes an operation input portion which is exposed to the outside, and which is configured to input a movement operation of moving the shaft along the movement axis and a rotation operation of rotating the shaft around the movement axis, and the operation input portion includes an input main body which is formed point-symmetrically with respect to the movement axis when seen from an axially parallel outward direction that is one of directions parallel to the movement axis, and an input projection which projects from the input main body toward a diametrically outer peripheral direction that is a direction departing from the movement axis in a plane perpendicular to the movement axis, the input projection forming the operation input portion so that the operation input portion has a shape which is point-asymmetrical with respect to the movement axis when seen from the axially parallel outward direction.

19. The endoscopic fluid passage changeover valve unit according to claim 18, wherein the operation input portion includes a first exposed surface facing in the axially parallel outward direction, and a second exposed surface facing in the diametrically outer peripheral direction, and the opening of the communication passage is opened to the outside in the second exposed surface in the input projection.

20. An endoscope comprising:

the endoscopic fluid passage changeover valve unit according to claim 1;

an operation section including a holding casing to which the cylinder portion of the endoscopic fluid passage changeover valve unit is fixedly attached; and an insertion section extending along a longitudinal axis in a part located to a distal direction side of the operation section.

\* \* \* \* \*